US012679895B2

(12) United States Patent
Qin et al.

(10) Patent No.: US 12,679,895 B2
(45) Date of Patent: Jul. 14, 2026

(54) RECOMBINANT ANTIBODY HAVING UNIQUE GLYCAN PROFILE PRODUCED BY CHO HOST CELL WITH EDITED GENOME AND PREPARATION METHOD THEREOF

(71) Applicant: Bio-Thera Solutions, Ltd., Guangzhou (CN)

(72) Inventors: Chao Qin, Guangzhou (CN); Yuanqing Zhou, Guangzhou (CN); Cuizhen Xiao, Guangzhou (CN)

(73) Assignee: Bio-Thera Solutions, Ltd., Guangzhou (CN)

( * ) Notice: Subject to any disclaimer, the term of this patent is extended or adjusted under 35 U.S.C. 154(b) by 733 days.

(21) Appl. No.: 18/050,970

(22) Filed: Oct. 28, 2022

(65) Prior Publication Data

US 2023/0203169 A1     Jun. 29, 2023

Related U.S. Application Data

(62) Division of application No. 16/337,371, filed as application No. PCT/CN2018/100008 on Aug. 10, 2018, now Pat. No. 11,505,609.

(30) Foreign Application Priority Data

Aug. 11, 2017    (CN) .......................... 201710687889.9

(51) Int. Cl.
| | |
|---|---|
| *C07K 16/28* | (2006.01) |
| *A61K 39/395* | (2006.01) |
| *C07K 16/30* | (2006.01) |
| *C12N 9/10* | (2006.01) |
| *C12N 15/62* | (2006.01) |

(52) U.S. Cl.
CPC ........ *C07K 16/2863* (2013.01); *A61K 39/395* (2013.01); *C07K 16/2887* (2013.01); *C07K 16/30* (2013.01); *C12N 9/1051* (2013.01); *C12N 15/62* (2013.01); *C07K 2317/40* (2013.01)

(58) Field of Classification Search
None
See application file for complete search history.

(56) References Cited

U.S. PATENT DOCUMENTS

| | | | |
|---|---|---|---|
| 2013/0058919 | A1 | 3/2013 | Lazar et al. |
| 2013/0326645 | A1 | 12/2013 | Cost et al. |
| 2014/0314748 | A1 | 10/2014 | Gokarn |

FOREIGN PATENT DOCUMENTS

| | | |
|---|---|---|
| CN | 102373214 A | 3/2012 |
| CN | 103865897 A | 6/2014 |
| CN | 103923215 A | 7/2014 |
| CN | 105392885 A | 3/2016 |
| CN | 106167525 A | 11/2016 |
| EP | 1688436 A1 | 9/2006 |
| JP | 2009523432 A | 6/2009 |
| JP | 2009526520 A | 7/2009 |
| WO | 2011116387 A1 | 9/2011 |
| WO | WO2012093833 A2 | 7/2012 |
| WO | 2013169398 A2 | 11/2013 |
| WO | 2015010114 A1 | 1/2015 |
| WO | WO2015193740 A2 | 12/2015 |
| WO | WO2016016842 A1 | 2/2016 |
| WO | 2017011773 A2 | 1/2017 |

OTHER PUBLICATIONS

Extended European Search Report Application No. 18842885.8-1111/3666891; PCT/CN201810008, Date of Completion of Search Jul. 7, 2021, Mailed Date, Jul. 16, 2021 (18 pages).
Sandra Cristea et al: "In vivo cleavage of transgene donors promotes nuclease-mediated targeted integration", Biotechnology and Bioengineering, vol. 110, No. 3, Mar. 1, 2013 (Mar. 1, 2013), pp. 871-880, XP055076901, DOI: 10.1002/bit.24733.
Yu et al: "Abstract 3823: Bat4306f, an anti-CD20 antibody devoid of fucose modification, demonstrates enhanced ADCC effect and potent in vivo efficacy: Cancer Research", Jul. 1, 2018 (Jul. 1, 2018), XP055821148, Retrieved from the internet: URL:https://cancerres.aacrjournals.org/cont ent/78/13Supplement/3823 [retrieved-on Jul. 5, 2021].
Yamane-Ohnuki N et al: "Establishment of FUT8 knockout chinese hamster ovary cells: an ideal host cell line for producing completely defucosylated antibodies with enhanced antibody-dependent cellular cytotoxicity", Biotechnology and Bioengineering, Wiley, US, vol. 87, No. 5, Aug. 6, 2004 (Aug. 6, 2004), pp. 614-622, XP002983758, ISSN: 0006-3592, DOI:10.1002/BIT.20151.
Katsuhiro Mori et al: "Non-fucosyl ated therapeutic antibodies: the next generation of therapeutic anti bodies", Cytotechnology, Kluwer Academic Publishers, DO, vol. 55, No. 2-3, Oct. 31, 2007 (Oct. 31, 2007), pp. 109-114, XP019550382, ISSN: 1573-0778, DOI: 10.1007/S10616-007-9103-2.
Sun "Using Crispr technology to knock out the FUT8 gene of CHO cells to produce completely fucose-free antibodies," Master's Thesis, Shanghai Jiaotong University, Pub: Jan. 4, 2017, Abstract. 1 page.

(Continued)

*Primary Examiner* — Ruixiang Li
(74) *Attorney, Agent, or Firm* — Sheppard Mullin Richter & Hampton LLP

(57) ABSTRACT

The present invention, in the field of bioengineering and biotechnology, relates to a method for preparing a recombinant antibody with a unique glycan profile produced by a genome-edited CHO host cell. Specifically, according to a method of the present invention, the TALEN technology is used to edit the FUT8 gene in CHO cells that have been adapted for serum-free suspension growth. The edited CHO host cells can produce recombinant antibodies with a unique glycan profile. The unique glycan profile can be characterized by non-fucosylated N-linked oligosaccharide chains of the antibodies, extremely low N-glycosylation heterogeneity and uniform carbohydrate chains. The antibody prepared by the method of the invention exhibit significantly increased ADCC and greater stability.

3 Claims, 8 Drawing Sheets

Specification includes a Sequence Listing.

(56)           References Cited

OTHER PUBLICATIONS

Anne-Laure Gagez et al: "Obinutuzumab: a new class of anti-CD20 monoclonal antibody" Current Opinion in Oncology, Sep. 2014 | vol. 26 | Issue 5 | pp. 484-491, Abstract. 1 page. doi:10.1097/CCO. 0000000000000107.

Masato Kinoshita, "Seminar: Genome Editing as Next-Generation Genetic Modification Technology—Focusing on Basic Principles", 2015, vol. 15, No. 4, pp. 305-309.

Bello et al., "Ofatumumab in the treatment of low-grade non-Hodgkin's lymphomas and chronic lymphocytic leukemia", Expert Rev. Clin. Immunol., 2011, 7(3), pp. 295-300.

Trastoy et al., "Structural basis of mammalian high-mannose N-glycan processing by human gut Bacteroides", Nature Communications, 2020, 11:899, 11 pages.

Cameron et al., "Obinutuzumab: First Global Approval", 2013, 10 pages.

Electrophoretogram for functional verification of TALEN protein

| Samples | Count | Volume (µL) | % of this plot | % of all | Mean FL1-A | CV FL1-A |
|---|---|---|---|---|---|---|
| CHO-BAT-KF | 2,000 | 3 | 100.00% | 53.18% | 5,022.27 | 101.65% |
| CHO-BAT | 2,000 | 14 | 100.00% | 64.96% | 901,836.94 | 137.30% |

Glycoscope Report: Glycoanalysis

| Sample Code | 7A4 | 7A5 | 7A6 | 7A7 |
|---|---|---|---|---|
| Customer Code | 41 | 43 | 1206 | Control |
| Table 1 | Value ± Error | Value ± Error | Value ± Error | Value ± Error |
| % Abundance in IgG-Fc Glycosylation | | | | |
| High Mannose | | | | |
| Total | 8 ± 3% | 10 ± 3% | 3 ± 1% | 3 ± 1% |
| Complex | | | | |
| Total | 92 ± 3% | 90 ± 3% | 97 ± 1% | 97 ± 1% |
| G0 | 92 ± 3% | 89 ± 3% | 86 ± 2% | 48 ± 4% |
| G1 | 0 ± 2% | 1 ± 2% | 11 ± 2% | 41 ± 3% |
| G2 | 0 ± 0% | 0 ± 0% | 0 ± 0% | 9 ± 2% |
| Antennae Termini | | | | |
| Sialic Acid | 0 ± 0% | 0 ± 0% | 0 ± 0% | 0 ± 0% |
| Gal alpha (1-3) Gal | 0 ± 0% | 0 ± 0% | 0 ± 0% | 0 ± 0% |
| Core Fucosylation | | | | |
| Total | 0 ± 5% | 10 ± 5% | 80 ± 5% | 81 ± 4% |

FIG. 5

| ☒Concensus | AAGATTCTTGCAAAGCTGGAGCGCTTAAA-CAACAAAATGAAGACTTGAGGAGAATGGCTGAGTCTCTCCGGTAGGTTTGAAATACTCAAG |
|---|---|
| 4 | 630    640    650    660    670    680    690    700    710 |
| 191-1.seq | AAGATTCTTGCAAAGCTGGAGCGCTTAAA--------ATGAAGACTTGAGGAGAATGGCTGAGTCTCTCCGGTAGGTTTGAAATACTCAAG |
| 191-2.seq | AAGATTCTTGCAAAGCTGGAGCGCTTAAAACAACAAAATGAAGACTTGAGGAGAATGGCTGAGTCTCTCCGGTAGGTTTGAAATACTCAAG |
| 217-1.seq | AAGATTCTTGCAAAGCTGGAGCGCTTAAA-CAACAAAATGAAGACTTGAGGAGAATGGCTGAGTCTCTCCGGTAGGTTTGAAATACTCAAG |
| 217-3.seq | AAGATTCTTGCAAAGCTGGAGCGCTTAAA-CAACAAAATGAAGACTTGAGGAGAATGGCTGAGTCTCTCGGGTAGGTTTGAAATACTCAAG |

FIG.6

| | BAT4306 | BAT4306F | Obinutuzumab | Rituximab |
|---|---|---|---|---|
| IC50 | 1.639 | 0.05641 | 0.1979 | 6.309 |

SEQUENCE LISTING

```
Sequence total quantity: 28
SEQ ID NO: 1              moltype = DNA   length = 21
FEATURE                  Location/Qualifiers
misc_feature             1..21
                         note = Synthetic
source                   1..21
                         mol_type = other DNA
                         organism = synthetic construct
SEQUENCE: 1
gggtagctaa ttgtctttca g                                          21

SEQ ID NO: 2              moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 2
taaatgccac tgcttctata                                            20

SEQ ID NO: 3              moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 3
tccaagattc ttgcaaagct                                            20

SEQ ID NO: 4              moltype = DNA   length = 18
FEATURE                  Location/Qualifiers
misc_feature             1..18
                         note = Synthetic
source                   1..18
                         mol_type = other DNA
                         organism = synthetic construct
SEQUENCE: 4
aatgaagact tgaggaga                                              18

SEQ ID NO: 5              moltype = DNA   length = 19
FEATURE                  Location/Qualifiers
misc_feature             1..19
                         note = Synthetic
source                   1..19
                         mol_type = other DNA
                         organism = synthetic construct
SEQUENCE: 5
ggagcgctta aaacaacaa                                             19

SEQ ID NO: 6              moltype = DNA   length = 763
FEATURE                  Location/Qualifiers
misc_feature             1..763
                         note = Synthetic
source                   1..763
```

-continued

```
                        mol_type = other DNA
                        organism = synthetic construct
SEQUENCE: 6
gggtagctaa ttgtctttca gcctcctggc caaagatacc atgaaagtca acttacgttg    60
tattctatat ctcaaacaac tcagggtgtt tcttactctt tccacagcat gtagagccca   120
ggaagcacag gacaagaaag ctgcctcctt gtatcaccag gaagatcttt ttgtaagagt   180
catcacagta taccagagag actaattttg tctgaagcat catgtgttga aacaacagaa   240
acttatttc ctgtgtggct aactagaacc agagtacaat gtttccaatt ctttgagctc    300
cgagaagaca gaagggagtt gaaactctga aaatgcgggc atggactggt tcctggcgtt   360
ggattatgct cattctttt gcctggggga ccttattgtt ttatataggt ggtcatttgg    420
ttcgagataa tgaccaccct gaccattcta gcagagaact ctccaagatt cttgcaaagc   480
tggagcgctt aaaacaacaa aatgaagact tgaggagaat ggctgagtct ctccggtagg   540
tttgaaatac tcaaggattt gatgaaatac tgtgcttgac ctttaggtat agggtctcag   600
tctgctgttg aaaaatataa tttctacaaa ccgtctttgt aaaattttaa gtattgtagc   660
agactttta aaagtcagtg atacatctat atagtcaata taggtttaca tagttgcaat   720
cttatttgc atatgaatca gtatatagaa gcagtggcat tta                     763

SEQ ID NO: 7          moltype = DNA   length = 204
FEATURE               Location/Qualifiers
misc_feature          1..204
                        note = Synthetic
source                1..204
                        mol_type = other DNA
                        organism = synthetic construct
SEQUENCE: 7
atgcgggcat ggactggttc ctggcgttgg attatgctca ttcttttgc ctgggggacc     60
ttattgtttt atataggtgg tcatttggtt cgagataatg accacctga ccattctagc    120
agagaactct ccaagattct tgcaaagctg gagcgcttaa aacaacaaaa tgaagacttg   180
aggagaatgg ctgagtctct ccgg                                          204

SEQ ID NO: 8          moltype = DNA   length = 1728
FEATURE               Location/Qualifiers
misc_feature          1..1728
                        note = Synthetic
source                1..1728
                        mol_type = other DNA
                        organism = synthetic construct
SEQUENCE: 8
atgcgggcat ggactggttc ctggcgttgg attatgctca ttcttttgc ctgggggacc     60
ttattgtttt atataggtgg tcatttggtt cgagataatg accacctga ccattctagc    120
agagaactct ccaagattct tgcaaagctg gagcgcttaa aacaacaaaa tgaagacttg   180
aggagaatgg ctgagtctct ccgaatacca gaaggcccta ttgatcaggg gacagctaca   240
ggaagagtcc gtgttttaga agaacagctt gttaaggcca aagaacagat tgaaaattac   300
aagaaacaag ctaggaatga tctgggaaag gatcatgaaa tcttaaggag gaggattgaa   360
aatggagcta aagagctctg gttttttcta caaagtgaat tgaagaaatt aaagaaatta   420
gaaggaaacg aactccaaag acatgcagat gaaattcttt tggatttagg acatcatgaa   480
aggtctatca tgacagatct atactacctc agtcaaacag atggagcagg tgagtggcgg   540
gaaaaagaag ccaaagatct gacagagctg gtccagcgga gaataacata tctgcagaat   600
cccaaggact gcagcaaagc cagaaagctg gtatgtaata tcaacaaagg ctgtggctat   660
ggatgtcaac tccatcatgt ggtttactgc ttcatgattg cttatggcac ccagcgaaca   720
ctcatcttgg aatctcagaa ttggcgctat gctactggag gatgggagac tgtgtttaa    780
cctgtaagtg agacatgcac agacaggtct ggcctctcca ctggacactg gtcaggtgaa   840
gtgaaggaca aaaatgttca agtggtcgag ctccccattg tagacagcct ccatcctcgt   900
cctcctact tacccttggc tgtaccagaa gaccttgcag atcgactcct gagagtccat   960
ggtgatcctg cagtgtggtg ggtatcccag tttgtcaaat acttgatccg tccacaacct  1020
tggctggaaa gggaaataga agaaccacc aagaagcttg gcttcaaaca tccagttatt   1080
ggagtccatg tcagacgcac tgacaaagtg ggaacagaag cagccttcca tcccattgag   1140
gaatacatgt tacacgttga agaacatttt cagcttctcg aacgcagaat gaaagtggat   1200
aaaaaagag tgtatctggc cactgtgac ccttctttgt taaaggaggc aaagacaaag    1260
tactccaatt atgaatttat tagtgataac tctatttctt ggtcagctgg actacacaac   1320
cgatacacag aaaattcact tcggggcgtg atcctggata tacactttct ctcccaggct   1380
gacttccttg tgtgtacttt ttcatcccag gtctgtaggg ttgcttatga aatcatgcaa   1440
acactgcatc ctgatgcctc tgcaaacttc cattctttag atgacatcta ctattttgga   1500
ggccaaaatg cccacaacca gattgcagtt tatcctcacc aacctcgaac taaagaggaa   1560
atccccatgg aacctggaga tatcattggt gtggctggaa accattggaa tggttactct   1620
aaaggtgtca acagaaaact aggaaaaaca ggcctgtacc cttcctacaa agtccgagag  1680
aagatagaaa cagtcaaata ccctacatat cctgaagctg aaaaatag                1728

SEQ ID NO: 9          moltype = AA   length = 575
FEATURE               Location/Qualifiers
REGION                1..575
                        note = Synthetic
source                1..575
                        mol_type = protein
                        organism = synthetic construct
SEQUENCE: 9
MRAWTGSWRW IMLILFAWGT LLFYIGGHLV RDNDHPDHSS RELSKILAKL ERLKQQNEDL    60
RRMAESLRIP EGPIDQGTAT GRVRVLEEQL VKAKEQIENY KKQARNDLGK DHEILRRRIE   120
NGAKELWFFL QSELKKLKKL EGNELQRHAD EILLDLGHHE RSIMTDLYYL SQTDGAGEWR   180
```

```
EKEAKDLTEL VQRRITYLQN PKDCSKARKL VCNINKGCGY GCQLHHVVYC FMIAYGTQRT   240
LILESQNWRY ATGGWETVFR PVSETCTDRS GLSTGHWSGE VKDKNVQVVE LPIVDSLHPR   300
PPYLPLAVPE DLADRLLRVH GDPAVWWVSQ FVKYLIRPQP WLEREIEETT KKLGFKHPVI   360
GVHVRRTDKV GTEAAFHPIE EYMVHVEEHF QLLERRMKVD KKRVYLATDD PSLLKEAKTK   420
YSNYEFISDN SISWSAGLHN RYTENSLRGV ILDIHFLSQA DFLVCTFSSQ VCRVAYEIMQ   480
TLHPDASANF HSLDDIYYFG GQNAHNQIAV YPHQPRTKEE IPMEPGDIIG VAGNHWNGYS   540
KGVNRKLGKT GLYPSYKVRE KIETVKYPTY PEAEK                              575

SEQ ID NO: 10             moltype = AA  length = 648
FEATURE                   Location/Qualifiers
REGION                    1..648
                          note = Synthetic
source                    1..648
                          mol_type = protein
                          organism = synthetic construct
SEQUENCE: 10
LTPEQVVAIA SHDGGKQALE TVQRLLPVLC QAHGLTPAQV VAIASHDGGK QALETVQRLL    60
PVLCQAHGLT PAQVVAIASN IGGKQALETV QRLLPVLCQA HGLTPDQVVA IASNIGGKQA   120
LETVQRLLPV LCQAHGLTPD QVVAIASNNG GKQALETVQR LLPVLCQAHG LTPDQVVAIA   180
SNIGGKQALE TVQRLLPVLC QAHGLTPDQV VAIASNGGGK QALETVQRLL PVLCQAHGLT   240
PAQVVAIASN GGGKQALETV QRLLPVLCQA HGLTPAQVVA IASHDGGKQA LETVQRLLPV   300
LCQAHGLTPA QVVAIASNGG GKQALETVQR LLPVLCQAHG LTPAQVVAIA SNGGGKQALE   360
TVQRLLPVLC QAHGLTPAQV VAIASNNGGK QALETVQRLL PVLCQAHGLT PDQVVAIASH   420
DGGKQALETV QRLLPVLCQA HGLTPAQVVA IASNIGGKQA LETVQRLLPV LCQAHGLTPD   480
QVVAIASNIG GKQALETVQR LLPVLCQAHG LTPDQVVAIA SNIGGKQALE TVQRLLPVLC   540
QAHGLTPDQV VAIASNNGGK QALETVQRLL PVLCQAHGLT PDQVVAIASH DGGKQALETV   600
QRLLPVLCQA HGLTPAQVVA IASNGGGRPA LESIVAQLSR PDPALAAL              648

SEQ ID NO: 11             moltype = AA  length = 580
FEATURE                   Location/Qualifiers
REGION                    1..580
                          note = Synthetic
source                    1..580
                          mol_type = protein
                          organism = synthetic construct
SEQUENCE: 11
LTPEQVVAIA SHDGGKQALE TVQRLLPVLC QAHGLTPAQV VAIASNGGGK QALETVQRLL    60
PVLCQAHGLT PAQVVAIASH DGGKQALETV QRLLPVLCQA HGLTPAQVVA IASHDGGKQA   120
LETVQRLLPV LCQAHGLTPA QVVAIASNGG GKQALETVQR LLPVLCQAHG LTPAQVVAIA   180
SHDGGKQALE TVQRLLPVLC QAHGLTPAQV VAIASNIGGK QALETVQRLL PVLCQAHGLT   240
PDQVVAIASN IGGKQALETV QRLLPVLCQA HGLTPDQVVA IASNNGGKQA LETVQRLLPV   300
LCQAHGLTPD QVVAIASNGG GKQALETVQR LLPVLCQAHG LTPAQVVAIA SHDGGKQALE   360
TVQRLLPVLC QAHGLTPAQV VAIASNGGGK QALETVQRLL PVLCQAHGLT PAQVVAIASN   420
GGGKQALETV QRLLPVLCQA HGLTPAQVVA IASHDGGKQA LETVQRLLPV LCQAHGLTPA   480
QVVAIASNIG GKQALETVQR LLPVLCQAHG LTPDQVVAIA SNGGGKQALE TVQRLLPVLC   540
QAHGLTPAQV VAIASNGGGR PALESIVAQL SRPDPALAAL                        580

SEQ ID NO: 12             moltype = DNA  length = 1944
FEATURE                   Location/Qualifiers
misc_feature              1..1944
                          note = Synthetic
source                    1..1944
                          mol_type = other DNA
                          organism = synthetic construct
SEQUENCE: 12
ctgaccccgg agcaggtggt ggccatcgct agtcatgacg gtggcaaaca ggctcttgag    60
accgtccaac gccttctacc agttctctgt caagcccacg gactaacccc agcgcaagtt   120
gtagcgattg ctagtcatga cggtggcaaa caggctcttg agaccgtcca acgccttcta   180
ccagttctct gtcaagccca cggactaacc ccagcgcaag ttgtagcgat tgctagtaat   240
attggtggca aacaggcact tgagacggtg cagcgcctcc ttccagttct ttgtcaagct   300
cacggactca ccccagatca agttgtagcg attgctagta atattggtgg caaacaggca   360
cttgagacgt tcagcgcct ccttccagtt ctttgtcaag ctcacggact caccccagat   420
caagttgtag cgattgctag taacaatggt ggcaaacagg ctctcgaaac cgtacaacga   480
ctcctcccag ttctctgtca agcccacgga ctaactcctg atcaagttgt agcgattgct   540
agtaatattg gtggcaaaca ggcacttgag acggttcagc gcctccttcc agttctttgt   600
caagctcacg gactcacccc agatcaagtt gtagcgattg ctagtaatgg gggtggcaaa   660
caggctcttg aaaccgtgca acgactgctc ccagttctct gtcaagccca cggcctcacc   720
ccggcgcaag ttgtagcgat tgctagtaat gggggtggca aacaggctct tgaaaccgtg   780
caacgactgc tcccagttct ctgtcaagcc cacggcctca ccccgggcga agttgtagcg   840
attgctagtc atgacggtgg caaacaggct cttgagaccg tccaacgcct tctaccagtt   900
ctctgtcaag cccacggact aaccccagcg caagttgtag cgattgctag taatgggggt   960
ggcaaacagg ctcttgaaac cgtgcaacga ctgctcccag ttctctgtca gcccacggc   1020
ctcaccccgg cgcaagttgt agcgattgct agtaatgggg gtggcaaaca ggctcttgaa   1080
accgtgcaac gactgctccc agttctctgt caagcccacg gcctcacccc gggcgcaagt   1140
gtagcgattg ctagtaacaa tggtggcaaa caggctctcg aaaccgtaca acgactcctc   1200
ccagttctct gtcaagccca cggactaact cctgatcaag ttgtagcgat tgctagtcat   1260
gacggtggca aacaggctct tgagaccgtc caacgccttc taccagttct ctgtcaagcc   1320
cacggactaa ccccagcgca agttgtagcg attgctagta atattggtgg caaacaggca   1380
cttgagacgt tcagcgcct ccttccagtt ctttgtcaag ctcacggact caccccagat   1440
```

```
caagttgtag cgattgctag taatattggt ggcaaacagg cacttgagac ggttcagcgc   1500
ctccttccag ttctttgtca agctcacgga ctcaccccag atcaagttgt agcgattgct   1560
agtaatattg gtggcaaaca ggcacttgag acggttcagc gcctccttcc agttctttgt   1620
caagctcacg gactcacccc agatcaagtt gtagcgattg ctagtaacaa tggtggcaaa   1680
caggctctcg aaaccgtaca acgactcctc ccagttctct gtcaagccca cggactaact   1740
cctgatcaag ttgtagcgat tgctagtcat gacggtggca aacaggctct tgagaccgtc   1800
caacgccttc taccagttct ctgtcaagcc cacggactaa ccccagcgca agttgtagcg   1860
attgctagta atggcggcgg tcgaccggcg ctggagagca ttgttgccca gttatctcgc   1920
cctgatccgg cgttggccgc gttg                                          1944
```

```
SEQ ID NO: 13              moltype = DNA   length = 1740
FEATURE                    Location/Qualifiers
misc_feature               1..1740
                           note = Synthetic
source                     1..1740
                           mol_type = other DNA
                           organism = synthetic construct
SEQUENCE: 13
ctgaccccgg agcaggtggt ggccatcgct agtcatgacg gtggcaaaca ggctcttgag   60
accgtccaac gccttctacc agttctctgt caagcccacg gactaacccc agcgcaagtt   120
gtagcgattg ctagtaatgg gggtggcaaa caggctcttg aaaccgtgca acgactgctc   180
ccagttctct gtcaagccca cggcctcacc ccggcgcaag ttgtagcgat tgctagtcat   240
gacggtggca aacaggctct tgagaccgtc caacgccttc taccagttct ctgtcaagcc   300
cacggactaa ccccagcgca agttgtagcg attgctagtc atgacggtgg caaacaggct   360
cttgagaccg tccaacgcct tctaccagtt ctctgtcaag cccacggact aaccccagcg   420
caagttgtag cgattgctag taatgggggt ggcaaacagg ctcttgaaac cgtgcaacga   480
ctgctcccag ttctctgtca gcccacggc ctcaccccgg cgcaagttgt agcgattgct   540
agtcatgacg gtggcaaaca ggctcttgag accgtccaac gccttctacc agttctctgt   600
caagcccacg gactaacccc agcgcaagtt gtagcgattg ctagtaatat tggtggcaaa   660
caggcacttg agacggttca gcgcctcctt ccagttcttt gtcaagctca cggactcacc   720
ccagatcaag ttgtagcgat tgctagtaat attggtggca aacaggcact tgagacgtc   780
cagcgcctcc ttccagttct ttgtcaagct cacggactca ccccagatca agttgtagcg   840
attgctagta acaatggtgg caaacaggct ctcgaaaccg tacaacgact cctcccagtt   900
ctctgtcaag cccacggact aactcctgat caagttgtag cgattgctag tcatgacggt   960
ggcaaacagg ctcttgaaac cgtgcaacga ctgctcccag ttctctgtca gcccacggc   1020
ctcaccccgg cgcaagttgt agcgattgct agtcatgacg gtggcaaaca ggctcttgag   1080
accgtccaac gccttctacc agttctctgt caagcccacg gactaacccc agcgcaagtt   1140
gtagcgattg ctagtaatgg gggtggcaaa caggctcttg aaaccgtgca acgactgctc   1200
ccagttctct gtcaagccca cggcctcacc ccggcgcaag ttgtagcgat tgctagtaat   1260
gggggtggca aacaggctct tgaaaccgtg caacgactgc tcccagttct ctgtcaagcc   1320
cacggcctca ccccggcgca agttgtagcg attgctagtc atgacggtgg caaacaggct   1380
cttgagaccg tccaacgcct tctaccagtt ctctgtcaag cccacggact aaccccagcg   1440
caagttgtag cgattgctag taatattggt ggcaaacagg cttcagcgc   1500
ctccttccag ttctttgtca agctcacgga ctcaccccag atcaagttgt agcgattgct   1560
agtaatgggg gtggcaaaca ggctcttgaa accgtgcaac gactgctccc agttctctgt   1620
caagcccacg gcctcacccc ggcgcaagtt gtagcgattg ctagtaatgg cggcggtcga   1680
ccggcgctgg agagcattgt tgcccagtta tctcgccctg atccggcgtt ggccgcgttg   1740
```

```
SEQ ID NO: 14              moltype = AA   length = 1072
FEATURE                    Location/Qualifiers
REGION                     1..1072
                           note = Synthetic
source                     1..1072
                           mol_type = protein
                           organism = synthetic construct
SEQUENCE: 14
MAPKKKRKVY PYDVPDYAGY PYDVPDYAGS YPYDVPDYAA HGTVDLRTLG YSQQQQEKIK   60
PKVRSTVAQH HEALVGHGFT HAHIVALSQH PAALGTVAVK YQDMIAALPE ATHEAIVGVG   120
KQWSGARALE ALLTVAGELR GPPLQLDTGQ LLKIAKRGGV TAVEAVHAWR NALTGAPLNL   180
TPEQVVAIAS HDGGKQALET VQRLLPVLCQ AHGLTPAQVV AIASHDGGKQ ALETVQRLLP   240
VLCQAHGLTP AQVVAIASNI GGKQALETVQ RLLPVLCQAH GLTPDQVVAI ASNIGGKQAL   300
ETVQRLLPVL CQAHGLTPDQ VVAIASNNGG KQALETVQRL LPVLCQAHGL TPDQVVAIAS   360
NIGGKQALET VQRLLPVLCQ AHGLTPDQVV AIASNGGKQ ALETVQRLLP VLCQAHGLTP   420
AQVVAIASNG GGKQALETVQ RLLPVLCQAH GLTPAQVVAI ASHDGGKQAL ETVQRLLPVL   480
CQAHGLTPAQ VVAIASNGGG KQALETVQRL LPVLCQAHGL TPAQVVAIAS NGGGKQALET   540
VQRLLPVLCQ AHGLTPAQVV AIASNNGGKQ ALETVQRLLP VLCQAHGLTP DQVVAIASHD   600
GGKQALETVQ RLLPVLCQAH GLTPAQVVAI ASNIGGKQAL ETVQRLLPVL CQAHGLTPDQ   660
VVAIASNIGG KQALETVQRL LPVLCQAHGL TPDQVVAIAS NGGGKQALET VQRLLPVLCQ   720
AHGLTPDQVV AIASNNGGKQ ALETVQRLLP VLCQAHGLTP DQVVAIASHD GGKQALETVQ   780
RLLPVLCQAH GLTPAQVVAI ASNGGGRPAL ESIVAQLSRP DPALAALTND HLVALACLGG   840
RPALDAVKKG LPHAPALIKR TNRRIPERTS HRVAGSQLVK SELEEKKSEL RHKLKYVPHE   900
YIELIEIARN PTQDRILEMK VMEFFMKVYG YRGEHLGGSR KPDGAIYTVG SPIDYGVIVD   960
TKAYSGGYNL PIGQAREMQR YVEENQTRNK HINPNEWWKV YPSSVTEFKF LFVSGHFKGN   1020
YKAQLTRLNH ITNCNGAVLS VEELLIGGEM IKAGTLTLEE VRRKFNNGEI NF           1072
```

```
SEQ ID NO: 15              moltype = DNA   length = 3216
FEATURE                    Location/Qualifiers
misc_feature               1..3216
                           note = Synthetic
```

-continued

```
source                  1..3216
                        mol_type = other DNA
                        organism = synthetic construct
SEQUENCE: 15
atggctccaa agaagaagcg taaggtatac ccatacgatg ttcctgacta tgcgggctat   60
ccctatgacg tcccggacta tgcaggatcg tatccatatg acgttccaga ttacgctgct  120
catggtaccg tggatctacg cacgctcggc tacagccagc agcaacagga gaagatcaaa  180
ccgaaggttc gttcgacagt ggcgcagcac cacgaggcac tggtcggcca cgggtttaca  240
cacgcgcaca tcgttgcgct cagccaacac ccggcagcgt tagggaccgt cgctgtcaag  300
tatcaggaca tgatcgcagc gttgccagag gcgacacacg aagcgatcgt tggcgtcggc  360
aaacagtggt ccggcgcacg cgctctggag gccttgctca cggtggcggg agagttgaga  420
ggtccaccgt tacagttgga cacaggccaa cttctcaaga ttgcaaaacg tggcggcgtg  480
accgcagtgg aggcagtgca tgcatggcgc aatgcactga cgggtgcccc cctgaacctg  540
accccgcagc aggtggttgc catcgctagt catgacggtg gcaaacaggc tcttgagacc  600
gtccaacgcc ttctaccagt tctctgtcaa gcccacggac taaccccagc gcaagttgta  660
gcgattgcta gtcatgacgg tggcaaacag gctcttgaga ccgtccaacg ccttctacca  720
gttctctgtc aagcccacgg actaacccca gcgcaagttg tagcgattgc tagtaatatt  780
ggtggcaaac aggcacttga gacggttcag cgcctccttc cagttctttg tcaagctcac  840
ggactcaccc cagatcaagt tgtagcgatt gctagtaata ttggtggcaa acaggcactt  900
gagacggttc agcgcctcct tccagttctt tgtcaagctc acggactcac cccagatcaa  960
gttgtagcga ttgctagtaa caatggtggc aaacaggctc tcgaaaccgt caacgactc  1020
ctcccagttc tctgtcaagc ccacggacta actcctgatc aagttgtagc gattgctagt  1080
aatattggtg gcaaacaggc acttgagacg gttcagcgcc tccttccagt tctttgtcaa  1140
gctcacggac tcaccccaga tcaagttgta gcgattgcta gtaatggggg tggcaaacag  1200
gctcttgaaa ccgtgcaacg actgctccca gttctctgtc aagcccacgg cctcaccccg  1260
gcgcaagttg tagcgattgc tagtaatggg ggtggcaaac aggctcttga aaccgtgcaa  1320
cgactgctcc cagttctctg tcaagcccac ggcctcaccc cggcgcaagt tgtagcgatt  1380
gctagtcatg acggtggcaa acaggctctt gagaccgtcc aacgccttct accagttctc  1440
tgtcaagccc acgactaac cccagcgcaa gttgtagcga ttgctagtaa tggggggtggc  1500
aaacaggctc ttgaaaccgt gcaacgactg ctcccagttc tctgtcaagc ccacggcctc  1560
accccggcgc aagttgtagc gattgctagt aatggggggtg gcaaacaggc tcttgaaacc  1620
gtgcaacgac tgctcccagt tctctgtcaa gcccacggcc tcaccccggc gcaagttgta  1680
gcgattgcta gtaacaatgg tggcaaacag gctctcgaaa ccgtacaacg actcctccca  1740
gttctctgtc aagcccacgg actaactcct gatcaagttg tagcgattgc tagtcatgac  1800
ggtggcaaac aggctcttga ccgtccaa cgccttctac cagttctctg tcaagcccac  1860
ggactaaccc cagcgcaagt tgtagcgatt gctagtaata ttggtggcaa acaggcactt  1920
gagacggttc agcgcctcct tccagttctt tgtcaagctc acggactcac cccagatcaa  1980
gttgtagcga ttgctagtaa tattggtggc aaacaggcac ttgagacggt tcagcgcctc  2040
cttccagttc tttgtcaagc tcacggactc accccagatc aagttgtagc gattgctagt  2100
aatattggtg gcaaacaggc acttgagacg gttcagcgcc tccttccagt tctttgtcaa  2160
gctcacggac tcaccccaga tcaagttgta gcgattgcta gtaacaatgg tggcaaacag  2220
gctctcgaaa ccgtacaacg actcctccca gttctctgtc aagcccacgg actaactcct  2280
gatcaagttg tagcgattgc tagtcatgac ggtggcaaac aggctcttga ccgtccaa  2340
cgccttctac cagttctctg tcaagcccac ggactaaccc cagcgcaagt tgtagcgatt  2400
gctagtaatg gcggcggtcg accggcgctg gagagcattg ttgcccagtt atctcgccct  2460
gatccggcgt tggccgcgtt gaccaacgac cacctcgtcg ccttggcctg cctcggcgga  2520
cgtcctgcgc tggatgcagt gaaaaaggga ttgccgcacg cccgtcttga tgatcaaaga  2580
accaatcgcc gtattcccga acgcacatcc catcgcgttg ccggatccca actagtcaaa  2640
agtgaactgg aggagaagaa atctgaactt cgtcataaat tgaaatatgt gcctcatgaa  2700
tatattgaat taattgaaat tgccagaaat cccactcagg atagaattct tgaaatgaag  2760
gtaatggaat tttttatgaa agtttatgga tatagaggtg agcatttggg tggatcaagg  2820
aaaccggacg gagcaattta tactgtcgga tctcctattg attacggtgt gatcgtggat  2880
actaaggctt atagcggagg ttataatctg ccaattggcc aagcacgaga aatgcaacga  2940
tatgtcgaag aaaatcaaac acgaaacaaa catatcaacc ctaatgaatg gtggaaagtc  3000
tatccatctt ctgtaacgga atttaagttt ttatttgtga gtggtcactt taaaggaaac  3060
tacaaagctc agcttacacg attaaatcat atcactaatt gtaatggagc tgttcttagt  3120
gtagaagagc ttttaattgg tggagaaatg attaaagccg gcacattaac cttagaggaa  3180
gtgagacgga aatttaataa cggcgagata aactttt                            3216

SEQ ID NO: 16              moltype = AA   length = 1004
FEATURE                    Location/Qualifiers
REGION                     1..1004
                           note = Synthetic
source                     1..1004
                           mol_type = protein
                           organism = synthetic construct
SEQUENCE: 16
MAPKKKRKVY PYDVPDYAGY PYDVPDYAGS YPYDVPDYAA HGTVDLRTLG YSQQQQEKIK   60
PKVRSTVAQH HEALVGHGFT HAHIVALSQH PAALGTVAVK YQDMIAALPE ATHEAIVGVG  120
KQWSGARALE ALLTVAGELR GPPLQLDTGQ LLKIAKRGGV TAVEAVHAWR NALTGAPLNL  180
TPEQVVAIAS HDGGKQALET VQRLLPVLCQ AHGLTPAQVV AIASNGGGKQ ALETVQRLLP  240
VLCQAHGLTP AQVVAIASHD GGKQALETVQ RLLPVLCQAH GLTPAQVVAI ASHDGGKQAL  300
ETVQRLLPVL CQAHGLTPAQ VVAIASNGGG KQALETVQPL PVLCQAHGL TPAQVVAIAS  360
HDGGKQALET VQRLLPVLCQ AHGLTPAQVV AIASNIGGKQ ALETVQRLLP VLCQAHGLTP  420
DQVVAIASNI GGKQALETVQ RLLPVLCQAH GLTPDQVVAI ASNNGGKQAL ETVQRLLPVL  480
CQAHGLTPDQ VVAIASNGGG KQALETVQRL LPVLCQAHGL TPAQVVAIAS HDGGKQALET  540
VQRLLPVLCQ AHGLTPAQVV AIASNGGGKQ ALETVQRLLP VLCQAHGLTP AQVVAIASNG  600
GGKQALETVQ RLLPVLCQAH GLTPAQVVAI ASHDGGKQAL ETVQRLLPVL CQAHGLTPAQ  660
VVAIASNIGG KQALETVQRL LPVLCQAHGL TPDQVVAIAS NGGGKQALET VQRLLPVLCQ  720
```

```
AHGLTPAQVV AIASNGGGRP ALESIVAQLS RPDPALAALT NDHLVALACL GGRPALDAVK    780
KGLPHAPALI KRTNRRIPER TSHRVAGSQL VKSELEEKKS ELRHKLKYVP HEYIELIEIA    840
RNPTQDRILE MKVMEFFMKV YGYRGEHLGG SRKPDGAIYT VGSPIDYGVI VDTKAYSGGY    900
NLPIGQADAM QSYVEENQTR NKHINPNEWW KVYPSSVTEF KFLFVSGHFK GNYKAQLTRL    960
NHITNCNGAV LSVEELLIGG EMIKAGTLTL EEVRRKFNNG EINF                    1004

SEQ ID NO: 17           moltype = DNA   length = 7114
FEATURE                 Location/Qualifiers
misc_feature            1..7114
                        note = Synthetic
source                  1..7114
                        mol_type = other DNA
                        organism = synthetic construct
SEQUENCE: 17
cgccattctg cctggggacg tcggagcaag cttgatttag gtgacactat agaatacaag    60
ctacttgttc tttttgcagg atctgccacc atggctccaa agaagaagcg taaggtatac   120
ccatacgatg ttcctgacta tgcgggctat ccctatgacg tcccggacta tgcaggatcg   180
tatccatatg acgttccaga ttacgctgct catggtaccg tggatctacg cacgctcggc   240
tacagccagc agcaacagga gaagatcaaa ccgaaggttc gttcgacagt ggcgcagcac   300
cacgaggcac tggtcggcca cgggtttaca cacgcgcaca tcgttgcgct cagccaacac   360
ccggcagcgt tagggaccgt cgctgtcaag tatcaggaca tgatcgcagc gttgccagag   420
gcgacacacg aagcgatcgt tggcgtcggc aaacagtggt ccggcgcacg cgctctggag   480
gccttgctca cggtggcggg agagttgaga ggtccaccgt tacagttgga cacaggccaa   540
cttctcaaga ttgcaaaacg tggcggcgtg accgcagtgg aggcagtgca tgcatggcgc   600
aatgcactga cgggtgcccc cctgaacctg accccggagc aggtggtggc catcgctagt   660
catgacggtg gcaaacaggc tcttgagacc gtccaacgcc ttctaccagt tctctgtcaa   720
gcccacggac taaccccagc gcaagttgta gcgattgcta gtaatggggg tggcaaacag   780
gctcttgaaa ccgtgcaacg actgctccca gttctctgtc aagcccacgg cctcaccccg   840
gcgcaagttg tagcgattgc tagtcatgac ggtggcaaac aggctcttga ccgtccaa    900
cgccttctac cagttctctg tcaagcccac ggactaaccc cagcgcaagt tgtagcgatt   960
gctagtcatg acggtggcaa acaggctctt gagaccgtcc aacgccttct accagttctc  1020
tgtcaagccc acggactaac cccagcgcaa gttgtagcga ttgctagtaa tggggggtggc  1080
aaacaggctc ttgaaaccgt gcaacgactg ctcccagttc tctgtcaagc ccacggcctc  1140
accccggcgc aagttgtagc gattgctagt catgacggtg gcaaacaggc tcttgagacc  1200
gtccaacgcc ttctaccagt tctctgtcaa gcccacggac taaccccagc gcaagttgta  1260
gcgattgcta gtaatattgg tggcaaacag gcacttgaga cggttcagcg cctccttcca  1320
gttctttgtc aagctcacgg actcacccca gatcaagttg tagcgattgc tagtaatatt  1380
ggtggcaaac aggcacttga cacggttcag cgcctccttc cagttctttg tcaagctcac  1440
ggactcaccc cagatcaagt tgtagcgatt gctagtaaca atggtggcaa acaggctctc  1500
gaaaccgtac aacgactcct cccagttctc tgtcaagccc acggactaac tcctgatcaa  1560
gttgtagcga ttgctagtaa tggggggtggc aaacaggctc ttgaaaccgt gcaacgactg  1620
ctcccagttc tctgtcaagc ccacggcctc accccggcgc aagttgtagc gattgctagt  1680
catgacggtg gcaaacaggc tcttgagacc gtccaacgcc ttctaccagt tctctgtcaa  1740
gcccacggac taaccccagc gcaagttgta gcgattgcta gtaatggggg tggcaaacag  1800
gctcttgaaa ccgtgcaacg actgctccca gttctctgtc aagcccacgg cctcaccccg  1860
gcgcaagttg tagcgattgc tagtaatggg ggtggcaaac aggctcttga aaccgtgcaa  1920
cgactgctcc cagttctctg tcaagcccac ggcctcaccc cggcgcaagt tgtagcgatt  1980
gctagtcatg acggtggcaa acaggctctt gagaccgtcc aacgccttct accagttctc  2040
tgtcaagccc acggactaac cccagcgcaa gttgtagcga ttgctagtaa tattggtggc  2100
aaacaggcac ttgagacggt tcagcgcctc cttccagttc tttgtcaagc tcacggactc  2160
accccggcgc aagttgtagc gattgctagt aatgggggtg gcaaacaggc tcttgaaacc  2220
gtgcaacgac tgctcccagt tctctgtcaa gcccacggcc tcaccccggc gcaagttgta  2280
gcgattgcta gtaatggcgg cggtcgaccg cgcgctggaga gcattgttgc ccagttatct  2340
cgccctgatc cggcgttggc cgcgttgacc aacgaccacc tcgtcgcctt ggcctgcctc  2400
ggcggacgtc ctgcgctgga tgcagtgaaa aagggattgc cgcacgcgcc ggccttgatc  2460
aaaagaacca atcgccgtat tcccgaacgc acatcccatc gcgttgccgg atcccaacta  2520
gtcaaaagtg aactggagga gaagaaatct gaacttcgtc ataaattgaa atatgtgcct  2580
catgaatata ttgaattaat tgaaattgcc agaaatccca ctcaggatag aattcttgaa  2640
atgaaggtaa tggaattttt tatgaaagtt tatggatata gaggtgagca tttgggtgga  2700
tcaaggaaac cggacggagc aatttatact gtcggatctc ctattgatta cggtgtgatc  2760
gtggatacta aagcttatag cggaggttat aatctgccaa ttggccaagc agatgccatg  2820
caaagctatg tcgaagaaaa tcaaacacga aacaaacata tcaaccctaa tgaatggtgg  2880
aaagtctatc catcttctgt aacggaattt aagtttttat ttgtgagtgg tcactttaaa  2940
ggaaactaca aagctcagct tacacgatta aatcatatca ctaattgtaa tggagctgtt  3000
cttagtgtag aagagctttt aattggtgga gaaatgatta agccggcac attaacctta  3060
gaggaagtga gacggaaatt taataacggc gagataaact tttaatctag aactatagtg  3120
agtcgtatta cgtagatcca gacatgataa gatacattga tgagtttgga caaaccacaa  3180
ctagaatgca gtgaaaaaaa tgctttattt gtgaaatttg tgatgctatt gctttatttg  3240
taaccattat aagctgcaat aaacaagtta acaacaacaa ttgcattcat tttatgtttc  3300
aggttcaggg ggaggtgtgg gaggtttttt aattcgcggc cgcggcgcca atgcattggg  3360
cccggtacgt acccagcttt tgttcccttt agtgagggtt aattgcgcgc ttggcgtaat  3420
catggtcata gctgtttcct gtgtgaaatt gttatccgct cacaattcca cacaacatac  3480
gagccggaag cataaagtgt aaagcctggg gtgcctaatg agtgagctaa ctcacattaa  3540
ttgcgttgcg ctcactgccc gctttccagt cgggaaacct gtcgtgccag ctgcattaat  3600
gaatcggcca acgcgcgggg agaggcggtt tgcgtattgg gcgctcttcc gcttcctcgc  3660
tcactgactc gctgcgctcg gtcgttcggc tgcggcgagc ggtatcagct cactcaaagg  3720
cggtaatacg gttatccaca gaatcagggg ataacgcagg aaagaacatg tgagcaaaag  3780
gccagcaaaa ggccaggaac cgtaaaaagg ccgcgttgct ggcgtttttc cataggctcc  3840
gcccccctga cgagcatcac aaaaatcgac gctcaagtca gaggtggcga aacccgacag  3900
```

-continued

```
gactataaag ataccaggcg tttcccctg gaagctccct cgtgcgctct cctgttccga    3960
ccctgccgct taccggatac ctgtccgcct ttctcccttc gggaagcgtg gcgctttctc    4020
atagctcacg ctgtaggtat ctcagttcgg tgtaggtcgt tcgctccaag ctgggctgtg    4080
tgcacgaacc ccccgttcag cccgaccgct gcgccttatc cggtaactat cgtcttgagt    4140
ccaacccggt aagacacgac ttatcgccac tggcagcagc cactggtaac aggattagca    4200
gagcgaggta tgtaggcggt gctacagagt tcttgaagtg gtggcctaac tacggctaca    4260
ctagaaggac agtatttggt atctgcgctc tgctgaagcc agttaccttc ggaaaaagag    4320
ttggtagctc ttgatccggc aaacaaacca ccgctggtag cggtggtttt tttgtttgca    4380
agcagcagat tacgcgcaga aaaaaaggat ctcaagaaga tcctttgatc ttttctacgg    4440
ggtctgacgc tcagtggaac gaaaactcac gttaagggat tttggtcatg agattatcaa    4500
aaaggatctt cacctagatc cttttaaatt aaaaatgaag ttttaaatca atctaaagta    4560
tatatgagta aacttggtct gacagttacc aatgcttaat cagtgaggca cctatctcag    4620
cgatctgtct atttcgttca tccatagttg cctgactccc cgtcgtgtag ataactacga    4680
tacgggaggg cttaccatct ggccccagtg ctgcaatgat accgcgagac ccacgctcac    4740
cggctccaga tttatcagca ataaaccagc cagccggaag ggccgagcgc agaagtggtc    4800
ctgcaacttt atccgcctcc atccagtcta ttaattgttg ccgggaagct agagtaagta    4860
gttcgccagt taatagtttg cgcaacgttg ttgccattgc tacaggcatc gtggtgtcac    4920
gctcgtcgtt tggtatggct tcattcagct ccggttccca acgatcaagg cgagttacat    4980
gatcccccat gttgtgcaaa aaagcggtta gctccttcgg tcctccgatc gttgtcagaa    5040
gtaagttggc cgcagtgtta tcactcatgg ttatggcagc actgcataat tctcttactg    5100
tcatgccatc cgtaagatgc ttttctgtga ctggtgagta ctcaaccaag tcattctgag    5160
aatagtgtat gcggcgaccg agttgctctt gcccggcgtc aatacgggat aataccgcgc    5220
cacatagcag aactttaaaa gtgctcatca ttggaaaacg ttcttcgggg cgaaaactct    5280
caaggatctt accgctgttg agatccagtt cgatgtaacc cactcgtgca cccaactgat    5340
cttcagcatc ttttactttc accagcgttt ctgggtgagc aaaaacagga aggcaaaatg    5400
ccgcaaaaaa gggaataagg gcgacacgga aatgttgaat actcatactc ttcctttttc    5460
aatattattg aagcatttat cagggttatt gtctcatgag cggatacata tttgaatgta    5520
tttagaaaaa taaacaaata ggggttccgc gcacatttcc ccgaaaagtg ccacctaaat    5580
tgtaagcgtt aatattttgt taaaattcgc gttaaatttt tgttaaatca gctcattttt    5640
taaccaatag gccgaaatcg gcaaaatccc ttataaatca aagaataga ccgagatagg    5700
gttgagtgtt gttccagttt ggaacaagag tccactatta agaacgtgg actccaacgt    5760
caaagggcga aaaaccgtct atcagggcga tggcccacta cgtgaaccat caccctaatc    5820
aagttttttg gggtcgaggt gccgtaaagc actaaatcgg aacctaaag ggagcccccg    5880
atttagagct tgacggggaa agccggcgaa cgtggcgaga aaggaaggga agaaagcgaa    5940
aggagcgggc gctagggcgc tggcaagtgt agcggtcacg ctgcgcgtaa ccaccacacc    6000
cgccgcgctt aatgcgccgc tacagggcgc gtcccattcg ccattcaggc tgcgcaactg    6060
ttgggaaggg cgatcggtgc gggcctcttc gctattacgc cagtcgatta tatactcgag    6120
atatatttcg accatagcca attcaatatg gcgtatatgg actcatgcca attcaatatg    6180
gtggatctgg acctgtgcca attcaatatg gcgtatatgg actcgtgcca attcaatatg    6240
gtggatctgg acccccagcca attcaatatg gcggacttgg caccatgcca attcaatatg    6300
gcggacttgg cactgtgcca actggggagg ggtctacttg gcacggtgcc aagtttgagg    6360
aggggtcttg gccctgtgcc aagtccgcca tattgaattg gcatggtgcc aataatggcg    6420
gccatattgg ctatatgcca ggatcaatat ataggcaata tccaatatgg ccctatgcca    6480
atatggctat tggccaggtt caatactatg tattggccct atgccatata gtattccata    6540
tatgggtttt cctattgacg tagatagccc ctcccaatgg gcggtcccat ataccatata    6600
tggggcttcc taataccgcc catagccact cccccattga cgtcaatggt ctctatatat    6660
ggtcttttcct attgacgtca tatggcggt cctattgacg tatatggcgc ctcccccatt    6720
gacgtcaatt acggtaaatg ccccgcctgg ctcaatgccc attgacgtca ataggaccac    6780
ccaccattga cgtcaatggg atggctcatt gcccattcat atccgttctc acgccccta    6840
ttgacgtcaa tgacggtaaa tggcccactt ggcagtacat caatatctat taatagtaac    6900
ttggcaagta cattactatt ggaaggacgc cagggtacat tggcagtact cccattgacg    6960
tcaatggcgg taaatggccc gcgatggctg ccaagtacat ccccattgac gtcaatgggg    7020
aggggcaatg acgcaaatgg gcgttccatt gacgtaaatg ggcggtaggc gtgcctaatg    7080
ggaggtctat ataagcaatg ctcgtttagg gaac                                 7114
```

SEQ ID NO: 18          moltype = AA  length = 213
FEATURE                Location/Qualifiers
REGION                 1..213
                       note = Synthetic
source                 1..213
                       mol_type = protein
                       organism = synthetic construct
SEQUENCE: 18
QIVLSQSPAI LSASPGEKVT MTCRASSSVS YIHWFQQKPG SSPKPWIYAT SNLASGVPVR    60
FSGSGSGTSY SLTISRVEAE DAATYYCQQW TSNPPTFGGG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                  213

SEQ ID NO: 19          moltype = AA  length = 451
FEATURE                Location/Qualifiers
REGION                 1..451
                       note = Synthetic
source                 1..451
                       mol_type = protein
                       organism = synthetic construct
SEQUENCE: 19
QVQLQQPGAE LVKPGASVKM SCKASGYTFT SYNMHWVKQT PGRGLEWIGA IYPGNGDTSY    60
NQKFKGKATL TADKSSSTAY MQLSSLTSED SAVYYCARST YYGGDWYFNV WGAGTTVTVS    120
AASTKGPSVF PLAPSSKSTS GGTAALGCLV KDYFPEPVTV SWNSGALTSG VHTFPAVLQS    180

```
SGLYSLSSVV TVPSSSLGTQ TYICNVNHKP SNTKVDKKAE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 20                moltype = AA   length = 113
FEATURE                      Location/Qualifiers
REGION                       1..113
                             note = Synthetic
source                       1..113
                             mol_type = protein
                             organism = synthetic construct
SEQUENCE: 20
DIVMTQTPLS LPVTPGEPAS ISCRSSKSLL HSNGITYLYW YLQKPGQSPQ LLIYQMSNLV   60
SGVPDRFSGS GSGTDFTLKI SRVEAEDVGV YYCAQNLELP YTFGGGTKVE IKR          113

SEQ ID NO: 21                moltype = AA   length = 449
FEATURE                      Location/Qualifiers
REGION                       1..449
                             note = Synthetic
source                       1..449
                             mol_type = protein
                             organism = synthetic construct
SEQUENCE: 21
QVQLVQSGAE VKKPGSSVKV SCKASGYAFS YSWINWVRQA PGQGLEWMGR IFPGDGDTDY   60
NGKFKGRVTI TADKSTSTAY MELSSLRSED TAVYYCARNV FDGYWLVYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 22                moltype = AA   length = 214
FEATURE                      Location/Qualifiers
REGION                       1..214
                             note = Synthetic
source                       1..214
                             mol_type = protein
                             organism = synthetic construct
SEQUENCE: 22
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPITFGQ GTRLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 23                moltype = AA   length = 452
FEATURE                      Location/Qualifiers
REGION                       1..452
                             note = Synthetic
source                       1..452
                             mol_type = protein
                             organism = synthetic construct
SEQUENCE: 23
EVQLVESGGG LVQPGRSLRL SCAASGFTFN DYAMHWVRQA PGKGLEWVST ISWNSGSIGY   60
ADSVKGRFTI SRDNAKKSLY LQMNSLRAED TALYYCAKDI QYGNYYYGMD VWGQGTTVTV   120
SSASTKGPSV FPLAPGSSKS TSGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 24                moltype = AA   length = 214
FEATURE                      Location/Qualifiers
REGION                       1..214
                             note = Synthetic
source                       1..214
                             mol_type = protein
                             organism = synthetic construct
SEQUENCE: 24
DIQMTQSPSS LSASVGDRVT ITCQASQDIS NYLNWYQQKP GKAPKLLIYD ASNLETGVPS   60
RFSGSGSGTD FTFTISSLQP EDIATYFCQH FDHLPLAFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 25                moltype = AA   length = 449
FEATURE                      Location/Qualifiers
```

-continued

```
REGION                    1..449
                          note = Synthetic
source                    1..449
                          mol_type = protein
                          organism = synthetic construct
SEQUENCE: 25
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTTVTVSSA  120
CTKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 26            moltype = AA   length = 214
FEATURE                  Location/Qualifiers
REGION                   1..214
                         note = Synthetic
source                   1..214
                         mol_type = protein
                         organism = synthetic construct
SEQUENCE: 26
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 27            moltype = AA   length = 451
FEATURE                  Location/Qualifiers
REGION                   1..451
                         note = Synthetic
source                   1..451
                         mol_type = protein
                         organism = synthetic construct
SEQUENCE: 27
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGTLVTVS  120
SCSTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 28            moltype = DNA   length = 203
FEATURE                  Location/Qualifiers
misc_feature             1..203
                         note = Synthetic
source                   1..203
                         mol_type = other DNA
                         organism = synthetic construct
SEQUENCE: 28
atgcgggcat ggactggttc ctggcgttgg attatgctca ttcttttttgc ctgggggacc  60
ttattgtttt atataggtgg tcatttggtt cgagataatg accaccctga ccattctagc  120
agagaactct ccaagattct tgcaaagctg gagcgcttaa acaacaaaat gaagacttga  180
ggagaatggc tgagtctctc cgg                                          203
```

RECOMBINANT ANTIBODY HAVING UNIQUE GLYCAN PROFILE PRODUCED BY CHO HOST CELL WITH EDITED GENOME AND PREPARATION METHOD THEREOF

CROSS REFERENCE TO RELATED APPLICATIONS

This application is a division of U.S. application Ser. No. 16/337,371, which is a national stage application of International Application PCT/CN2018/100008, filed Aug. 10, 2018 which claims priority to Chinese Application No. 201710687889.9, filed Aug. 11, 2017, the content of each of which is hereby incorporated by reference in its entirety.

REFERENCE TO AN ELECTRONIC SEQUENCE LISTING

The contents of the electronic sequence listing (292919.xml; Size: 59,673 bytes; and Date of Creation: Oct. 28, 2022) is herein incorporated by reference in its entirety.

TECHNICAL FIELD

The present invention belongs to the field of bioengineering and biotechnology, and relates to a class of recombinant antibodies with a unique glycan profile produced by a genome-edited CHO host cells and preparation methods for the host cells and antibodies.

BACKGROUND ART

CHO cells (Chinese Hamster Ovary, CHO) are epithelial anchorage-dependent cells extensively used in bioengineering at present, which were first isolated from the ovary of an adult female hamster in 1957 by Dr. Theodore T. Puck from the University of Colorado. CHO-K1 cells are widely used in industrial production. As transformed cell lines, such cells are hypodiploid cells having the chromosome distribution frequency 2n=22. The CHO-K1 cell lines (No. CCL-61), which are preserved by ATCC, have been widely used to express the recombinant DNA protein. The original cells are anchorage-dependent cells and can also grow in suspension after multiple passages and screening. CHO cells are prone to gene mutation and gene transfection. Early studies also demonstrated that, compared with other engineering cell lines, antibodies produced by the CHO cells have the most similar glycotype to the human serum antibodies; thus the CHO cells are good host cells for mammalian gene expression.

The mechanism of therapeutic antibodies is to form a complex with the target molecule, causing neutralization of the target antigen or eliminating the antigen or pathogen through the immunological effect of the Fc fragment of the antibody. The specific binding ability of antibody drugs to target molecules as well as their activity depend on their complex multi-level structure and post-translational modification; moreover, as the most important post-translational modification of antibody, glycosylation plays an important role in the biological activity, metabolism and immunogenicity of the antibodies. The glycosylation forms of antibody drugs are mainly N-glycosylation, involving such monosaccharides as glucose, galactose, mannose, N-acetylglucosamine, N-acetylgalactosamine, fucose and sialic acid (NANA, NGNA). Based on the amount of terminal galactose, the two-branched or multi-branched double-antenna complex oligosaccharides connected to Fc fragment Asn297 of the antibody molecule can be divided into G0, G1 (1, 3), G1 (1, 6) and G2, and each type can be further divided into 16 subtypes according to the presence of fucose (F) or bisected galactose (B) (Glycobiology, Volume 25, Issue 12, December 2015, Pages 1325-1334). Therefore, there are at least 36 types of oligosaccharides of the antibody heavy chain, even without considering terminal sialylation or high mannose; meanwhile, as the two heavy chains of the antibody can be randomly combined to form up to 400 different glycotypes, the antibody shows high heterogeneity.

Different glycotypes have different effects on the pharmaceutical properties of therapeutic antibodies. High mannose (Man5) results in rapid elimination of antibodies in blood and shortens half-life (MAbs, 2012, 4 (4): 509-520). G0F promotes complement pathway and accelerates elimination rate. The content of G2F increases in pregnant women and neonatal umbilical cords. Sialic acid modification has a significant effect on the inflammation of intravenous immunoglobulin. A decrease of fucose results in a significant increase of ADCC activity (JBC (2003) Chemistry 278, 3466-3473). Therefore, it is necessary to design and optimize the carbohydrate chain of therapeutic antibodies according to their main mechanism of action and therapeutic use.

Unlike protein expression, the glycosylation of the antibodies does not have a template to follow, and its glycosylation type and proportion of oligosaccharide components are affected by the host cell type and culture conditions. Methods of modifying the oligosaccharide components of monoclonal antibodies by engineering host cells to enhance their Fc-mediated effects are scattered in different literatures and patents. For example, antibodies prepared with the CHO cells overexpressed with $\beta(1,4)$-N-acetylglucosaminyltransferase III (GnT III) have higher ADCC activity than those expressed in parent cells, and the difference in activity is about 10 to 20 times (Bio Technol Bioeng. (2001) August 20; 74 (4): 288-94). However, the overexpression of GnT III is toxic to the CHO cells and the expression quantity of GnT III tends to decrease as heterogeneous expression increases with the passage number in the culture process. The fucose content of antibodies produced by using GnT III as host cells will change, thus affecting the uniformity of antibody drugs. Examples of the cell lines producing nonfucosylated antibodies also include Lec13 CHO cells with protein fucosylation defects (Ripka et al. Arch. Biochem. Biophys. 249: 533-545 (1986)), but they are not suitable as the host cells for the production of therapeutic antibodies due to their extremely low protein production (Yutaka Kanda et al. Biotechnol Bioeng. (2006) July 5; 94(4):680-8). CHO cells (Yamane-Ohnuki et al. (2004), Biotech. Bioeng. 87:614) with $\alpha$-1-6 fucosyltransferase gene FUT8 knocked out also result in a decrease in the production of antibody fucose. In FUT8 knockout cell lines as described in Yamane-Ohnuki and Kyowa Hakko patents, a method for controlling antibody fucose level and improving ADCC (antibody-dependent cell-mediated cytotoxicity) effect is disclosed. According to this method, the expression of FUT8 gene in a host cell is inhibited by a specific siRNA so as to reduce the fucose level of antibodies produced by the host cell. However, this method has the same disadvantages as the CHO cell lines overexpressing GnT III described above. First, the host cells have to be introduced with exogenous sequences; second, only up to about 70% of target genes can be inhibited by siRNA; and finally, the stability of siRNA expression may affect the quality properties of antibody drugs.

Recently, new genome editing techniques used for editing host cell target genes, inactivating the FUT8 enzyme in the cell and lowering the fucose level of antibody have been reported repeatedly in different literatures and patents. For example, Malphettes et al. (2010) reported that parent cells DG44 were knocked out by the zinc finger nuclease (ZFN) technology to obtain the homozygous FUT8 gene knockout DG44 derivative clone, and the antibody produced by this cell line was completely free of fucose. Beurdeley et al. (2012) reported that the FUT8 gene of CHO-K1 cells was edited by the TALEN technology, resulting in the loss of FUT8 enzyme activity in the host cells. Again, Sun et al. (2015) reported that editing exon 10 of FUT8 gene by the CRISPR/Cas9 technology resulted in loss of FUT8 enzyme activity in CHO-K1 cells.

SUMMARY OF THE INVENTION

In view of the problems that although the existing antibody drugs are basically limited to single N-glycosylation modification of Fc, the production stability is affected by inconsistent and easily changing glycotype components and contents, it is necessary to provide antibodies with a unique glycan profile produced by genome-edited CHO host cells, and methods for preparing the antibodies. The purpose of the present invention is achieved by the following technical means:

In a first aspect, the present invention provides a pair of polypeptides comprising the amino acid sequences as shown in SEQ ID NO. 10 and SEQ ID NO. 11, or comprising at least 90%, at least 91%, at least 92%, at least 93%, at least 94%, at least 95%, at least 96%, at least 97%, at least 98% or at least 99% sequence identity to the sequences as shown in SEQ ID NO. 10 and SEQ ID NO. 11. In some embodiments, the pair of polypeptides as shown in SEQ. NO. 10 and SEQ. NO. 11 have the amino acid sequence of the DNA binding domains upstream and downstream of TALEN respectively, and can specifically bind specific base zones of genes.

In a second aspect, the present invention provides a pair of polynucleotides encoding the pair of polypeptides as shown in SEQ. NO. 10 and SEQ. NO. 11, respectively. In some embodiments, the pair of polynucleotides comprise the nucleic acid sequences as shown in SEQ ID NO. 12 and SEQ ID NO. 13, or comprise at least 90%, at least 91%, at least 92%, at least 93%, at least 94%, at least 95%, at least 96%, at least 97%, at least 98% or at least 99% sequence identity to the sequences as shown in SEQ ID NO. 12 and SEQ ID NO. 13.

In a third aspect, the present invention provides a pair of fusion proteins formed by fusing a pair of polypeptides described above to the amino acid sequence of a DNA cleavage domain of a transcriptional activator-like effector (FokI). In some embodiments, the amino acid sequence of the DNA cleavage domain of the transcription activator-like effector (FokI) is natural or artificially modified. In some embodiments, the pair of fusion proteins comprise the amino acid sequences as shown in SEQ ID NO. 14 and SEQ ID NO. 16, or comprise at least 90%, at least 91%, at least 92%, at least 93%, at least 94%, at least 95%, at least 96%, at least 97%, at least 98% or at least 99% sequence identity to the sequences as shown in SEQ ID NO. 14 and SEQ ID NO. 16. In some embodiments, the pair of fusion proteins can specifically recognize two nucleotide sequences of CHO's FUT8 gene. In some embodiments, the two nucleotide sequences of CHO's FUT8 gene are located on the exon 1 (Exon1, SEQ ID NO. 7) of the FUT8 gene. In some embodiments, the two nucleotide sequences of the FUT8 gene comprise the nucleotide sequences as shown in SEQ ID NO. 3 and SEQ ID NO. 4 respectively. In some embodiments, a Space between the nucleotide sequences as shown in SEQ ID NO. 3 and SEQ ID NO. 4 comprise the sequence as shown in SEQ ID NO. 5.

In a fourth aspect, the present invention also provides a pair of nucleotides encoding the pair of fusion proteins respectively. In some preferred embodiments, the pair of nucleotide comprise the nucleic acid sequences as shown in SEQ ID NO. 15 and SEQ ID NO. 17, or comprise at least 90%, at least 91%, at least 92%, at least 93%, at least 94%, at least 95%, at least 96%, at least 97%, at least 98% or at least 99% sequence identity to the sequences as shown in SEQ ID NO. 15 and SEQ ID NO. 17.

In a fifth aspect, the present invention also provides a vector of at least any one polynucleotide of the pair of polynucleotides. In some embodiments, the vector is a plasmid.

In a sixth aspect, the present invention also provides host cells transfected with the vector.

In some embodiments, these cells transfected with the vector are the genome-edited CHO host cells, and their parent cells are derived from the CHO-K1 cell lines.

In some embodiments, parent cells of genome-edited CHO host cells are adapted to serum-free suspension culture; and the parent cells are named as CHO-BAT.

In some embodiments, the parent cells CHO-BAT of the genome-edited CHO host cells are a subclone of CHO-K1 selected to satisfy one or more of the following characteristics:

The cells have high transfection efficiency;

The cells have a short exponential growth time;

The cells have the ability to achieve a high cell density in the CD-CHO culture.

In some embodiments, compared with the parent cells, the genome-edited CHO host cells cause the endogenous α-1, 6-fucosyltransferase (FUT8) to lose its enzymatic activity due to the base deletion, insertion and nonsense mutation in certain zones of the FUT8 gene.

The cells do not contain exogenous DNA sequences;

The cells as host cells express recombinant antibodies having unique glycan profile characteristics.

In some embodiments, the genome-edited CHO host cells are characterized in that the genome of exon 1 of the FUT8 gene of the cells is edited, causing the endogenous FUT8 of the cells to loss enzyme activity; and the cells do not contain the DNA sequence of the expression vector introduced in the process of causing base deletion and unintentional mutation of the FUT8 gene;

The cells as host cells express recombinant antibodies having unique glycan profile characteristics are characterized by having non-fucosylated N-linked oligosaccharide and other glycan profile characteristics of the antibodies.

In some embodiments, the FUT8 gene of the genome-edited CHO host cells is knocked out, the cells' lectin LCA binding is negative, and the cells are named as CHO-BAT-KF.

In a seventh aspect, the present invention provides a kit comprising at least any one polypeptide of the pair of polypeptides, or at least any one polynucleotide of the pair of polynucleotides, or at least any one fusion protein of the pair of fusion proteins, or the vector, or the host cell.

In an eighth aspect, the present invention provides a use of the pair of polypeptides/polynucleotides/fusion proteins, or the vector in the FUT8 gene-edited CHO cells.

In a ninth aspect, the present invention provides a use of the pair of polypeptides/polynucleotides/fusion proteins, or the vector or the host cell in the production of antibodies, especially the antibodies with unique glycan profile, or provides the antibodies produced by the pair of polypeptides/polynucleotides/fusion proteins, or the vector or the host cell.

In a tenth aspect, the present invention provides a method for editing the FUT8 gene of CHO, comprising the following steps: transferring the pair of fusion proteins or the pair of polynucleotides or the vector into the CHO cells, incubating at 37° C. for 14 days, and obtaining the FUT8 gene knockout CHO cells through pressure screening and limited dilution. Refer to Wood et al., J Immunol. 145:3011 (1990) for exemplary methods.

In an eleventh aspect, the present invention provides a method for preparing a recombinant antibody with a unique glycan profile produced by genome-edited CHO host cells, comprising the following steps:

(1) transfecting the CHO cells (e.g. wild-type CHO cells) with the pair of fusion proteins or the pair of polynucleotides or the vector, and obtaining the FUT8 gene knockout CHO cells through pressure screening and limited dilution;

(2) electrically transfecting the FUT8 gene knockout CHO cells with the plasmid encoding the antibody gene expression cassette, and obtaining stable CHO cell lines secreting antibodies through pressure screening and limited dilution;

as a preferred embodiment, the vector is transfected into wild-type CHO cells described in step (1); more preferably, the plasmid is stably transfected into wild-type CHO cells;

as a preferred embodiment, the CHO cell is CHO-K1; more preferably, the CHO-K1 is adapted to serum-free culture.

As a preferred embodiment, the antibody is an anti-CD20 antibody; more preferably, the antibody is a humanized or full human anti-CD20 antibody; more preferably, the antibody is BAT4306F; more preferably, the antibody BAT4306F comprises two light chains as shown in SEQ ID NO. 20 and two heavy chains as shown in SEQ ID NO. 21. The inventor has adopted the method, cells, polypeptides and the like of the present invention to prepare various types of antibodies. It is found through research that different types of the prepared antibodies all show highly consistent glycotype and low heterogeneity, which means that the method, cells and the like of the present invention are suitable for the preparation of all types of antibodies. In one embodiment, the antibody binds CD20. In one embodiment, the CD20 binding antibody is a humanized antibody. In a preferred embodiment, the humanized antibody BAT4306F has a heavy chain variable zone B-HH6 amino acid sequence and a light chain variable zone B-KV1 amino acid sequence from the B-Ly1 antibody sequence in WO2005044859. BAT4306F antibody comprises a pair of light and heavy chains of the following sequences: SEQ ID NO. 20 and SEQ ID NO. 21. In one embodiment, the CD20 binding antibody is a full human antibody BAT4406F, which comprises a pair of light and heavy chains of the following sequences: SEQ ID NO. 22 and SEQ ID NO. 23. In one embodiment, the antibody is BAT1206F, and the BAT1206F antibody comprises two light chains as shown in SEQ ID NO. 18 and two heavy chains as shown in SEQ ID NO. 19. In one embodiment, the antibody is BAT0206F, and BAT0206F binds to EGFR, and comprises two light chains as shown in SEQ ID NO. 24 and two heavy chains as shown in SEQ ID NO. 25. In one embodiment, the antibody is BAT0808, and BAT0808 binds to Trop2, and comprises two light chains as shown in SEQ ID NO. 26 and two heavy chains as shown in SEQ ID NO. 27. In some embodiments, the modified glycoprotein is secreted by a host cell. In some embodiments, the modified glycoprotein is an antibody.

As an exemplary embodiment, the present invention provides a method for preparing a recombinant antibody with unique glycan profile produced by the genome-edited CHO host cell or an antibody produced by the method, comprising the following specific steps:

Transfect the pair of fusion proteins or the pair of polynucleotides or the vector into the wild-type CHO cells, adding CD CHO (Sigma)+10% FBS (fetal calf serum) containing phytohemagglutinin (LCA) into the transfected cells and perform the pressure screening; after 14 days, seed the surviving cells into a 96-well cell culture plate at 0.5 cells/well, and decrease the serum concentration to 5%; after 7 days, transfer the cells into a 24-well cell culture plate, incubate in a 37° C. CO$_2$ incubator for 7 days. Then, take out some cells, centrifuge at 1000 rpm for 5 min, resuspend in PBS, mix 2 μl of fluorescein labeled LCA with the cells, and incubating on ice for 30 min. Next, wash the cells with PBS once and read fluorescence on a flow cytometry (BD, C6); take the untransfected wild-type CHO cells as negative control. Transfer positive cells to a 6-well cell culture plate, and decrease the serum concentration to 1%; after 7 days, transfer cells to a small shake flask, and taking serum-free CD CHO as the medium. Then, the domestication process is completed. Use a plasmid extraction kit (Omega) to extract the CHO genome from some cells. By taking the genome as a template, carry out the polymerase chain reaction (PCR) with the primers L130 for (SEQ ID NO. 1), L130rev (SEQ ID NO. 2) and taq enzyme, and catalyzes the joining of the PCR product and T-vector (Promega), transform into E. coli competent cells, and coat plates. On the next day, pick single colonies, and sequence with T7 primer. Analyze the sequences by the DNASTAR analysis software, compared with the wild-type CHO genome sequence, colony with base deletions expands in culture and is named as CHO-BAT-KF. Establish a cell bank for CHO-BAT-KF when the cells being at logarithmic growth phase, and freezing the cells with CD CHO cryoprotectant containing 7.5% of DMSO, and transfer them to a liquid nitrogen tank for long-term storage. Linearize the plasmid encoding the antibody gene, measure OD260, mix 50 μg of plasmid with 10$^7$ CHO-BAT-KF in electric rotor, transfect with an electroporator (Biorad), seed the cell into a 96-well cell culture plate, and add methionine sulfoximine (MSX) after 48 h. After 14 days, coat the ELISA plate with an anti-FC multi-antibody; after blocking with 3% BSA, add supernatant to the plate and incubate at 37° C. for 2 h. Wash with PBST for 5 times, add anti-HRP labeled goat anti-human kappa/lambda light chain, 2M H$_2$SO$_4$, and read OD450 value on a microplate reader. The colonies with high titer are expanded, and the cell supernatant is collected by centrifugation to obtain the fucose-knocked antibody protein.

The present invention also provides a cell, which is a genome-edited CHO host cell.

The edited FUT8 gene of the genome-edited CHO host cells described above comprise the sequence as shown in SEQ ID NO. 28, or the sequence comprising at least 90%, at least 91%, at least 92%, at least 93%, at least 94%, at least 95%, at least 96%, at least 97%, at least 98%, at least 99%, at least 99.5%, or at least 99.8% sequence identity to the sequence as shown in SEQ ID NO. 28.

The present invention also provides a nucleic acid comprising a sequence as shown in SEQ ID NO. 28, or a nucleic acid comprising at least 90%, at least 91%, at least 92%, at least 93%, at least 94%, at least 95%, at least 96%, at least 97%, at least 98%, at least 99%, at least 99.5%, or at least 99.8% sequence identity to the sequence as shown in SEQ ID NO. 28.

The invention also provides a CHO host cell preserved in China Center for Type Culture Collection (CCTCC NO: C2017127; date: Aug. 10, 2017; address: Wuhan University, Wuhan, China; classified designation: CHO-BAT-KF FUT8 (–/–)).

In some embodiments, the host cell is kept in a serum-free medium. In some embodiments, the host cell is kept in a suspension culture. The invention also relates to a medium containing the host cells and a culture fermenter containing multiple host cells in the medium. In some embodiments, the medium is serum-free.

In a twelfth aspect, the present invention provides an antibody, which is a recombinant antibody with a unique glycan profile produced by the genome-edited CHO host cell. The antibody is a humanized or full human antibody having a unique glycosylation mode, a low heterogeneity of N-glycosylation and a significantly increased ADCC effect.

In some embodiments, the recombinant antibody with a unique glycan profile produced by the genome-edited CHO host cell is a humanized antibody binding CD20 on the cell membrane surface.

In some embodiments, the recombinant antibody with a unique glycan profile produced by the genome-edited CHO host cell has a unique glycosylation mode characterized in a change in the level of one or more saccharide fractions of the antibody N-linked polysaccharide has a unique glycosylation mode, wherein the saccharide fractions are selected from glucose (Glc), fucose (Fuc), galactose (Gal), mannose (Man), high mannose, glucosamine, G0 and acetylglucosamine (GlcNAc). The characteristics of glycosylation mode satisfy one or more of the following preferred conditions:

The fucose content of the antibody is very low; (0-5%)
The galactose level of the antibody is low; (≤30%)
The mannose level of the antibody is low; (≤5%)
The high mannose level of the antibody is low; (≤5%)
The G0 level of the antibody is high. (≥60%)
In some embodiments, the antibody has a low galactose level, ≤5%.

In some embodiments, the antibody has a high G0 level, ≥80%.

In some embodiments, the recombinant antibody with a unique glycan profile produced by the genome-edited CHO host cell satisfies the preferred condition that the fucose content is 0.

In some embodiments, the recombinant antibody with a unique glycan profile produced by the genome-edited CHO host cell has extremely low heterogeneity of N-polysaccharide and uniform carbohydrate chain.

In some embodiments, the recombinant antibody with a unique glycan profile produced by the genome-edited CHO host cell has a strong ADCC effect of Fc.

In some embodiments, the antibody has a glycan profile as shown for BAT4306F in the upper FIG. 10 of the Specification.

In some embodiments, the BAT4306F comprises two light chains as shown in SEQ ID NO. 20 and two heavy chains as shown in SEQ ID NO. 21; however, it is not excluded that these sequences are mutated as long as these mutations do not affect the function of the antibody.

In a thirteenth aspect, the present invention provides a FUT8 gene knockout CHO host cell, and the first exon of the FUT8 gene in this CHO host cell contains an inactivating mutation. This mutation may be one or more amino acid substitutions or deletions, or a frameshift mutation as shown in FIG. 6.

The present invention also provides a pharmaceutical composition comprising the antibody. As a preferred embodiment, the pharmaceutical composition also contains a pharmaceutically acceptable carrier.

The present invention also provides a method for preventing/treating a disease, comprising administering an effective amount of the antibody/fragment thereof disclosed herein to a subject in need thereof. In some embodiments, the disease is selected from the group consisting of cancer, anaphylaxis, cardiovascular disease, inflammatory disease, metabolic disease, neurological disease, viral infection, and/or bacterial infection. For example, the disease may be cancer or anaphylaxis. In some embodiments, the subject is mammal, such as a human being.

Compared with the existing antibody drugs, the present invention has the following advantages:

At present, the marketed antibody drugs are basically limited to the single N-glycosylation modification of Fc, however, due to inconsistent glycotype compositions and contents and easy changes, are complicated to a certain extent, especially posing a challenge to their stable production. According to the present invention, the recombinant antibody with unique glycan profile produced by the genome-edited CHO host cell has low N-glycosylation heterogeneity and good carbohydrate chain uniformity; at the same time, its ADCC effect is enhanced, and thus it greatly improves the quality and pharmaceutical properties of antibody drugs.

Compared with the corresponding antibody produced by the unmodified CHO-K1 (ATCC #CCL-61) or suspension-adapted parent cell CHO-BAT, the binding affinity of the antibody to the FcγRIIIA receptor is increased.

The modified host cells produce antibodies that have an enhanced affinity for FcγRIIIA compared with the corresponding antibodies produced by the unmodified host cells.

BRIEF DESCRIPTION OF THE DRAWINGS

FIG. 5 shows the carbohydrate chain chip analysis, wherein the fucose content of the submitted gene-edited clones 41 and 43 is reduced to 0-10%, while the fucose content of the wild-type antibody 1206 is 80%.

FIG. 6 shows the sequencing of the target sequence of TALEN protein after PCR amplification, with the results being compared by the lasergeneMegAlign sequence analysis software. 191-1, 191-2, 217-1, 217-3 are four selected clones with regulated genomes. Genomes were extracted as DNA templates, PCR reaction was performed with primers L130 for and L130rev, and CEL-1 base mismatch analysis was performed on the amplification products. The results show that cell clones 191-1 and 191-2 were heterozygous and cell clones 217-1 and 217-3 were homozygous. According to the comparison of results, the genome-edited homozygote 217-1 and 217-3 were selected and designated as CHO-2G8 and CHO-1D6. CHO-2G8 was finally selected as the host cell for subsequent experiments, and the host cell was named as CHO-BAT-KF.

Figure 1:
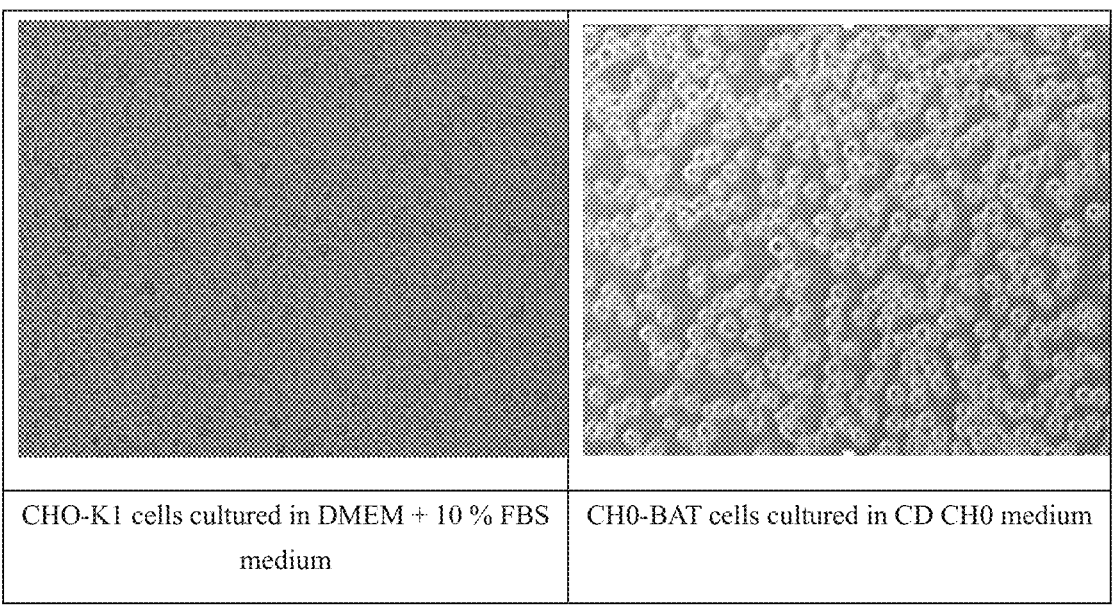
FIG. 1 shows an anchorage-dependent CHO-K1(ATCC #CCL-61) and a CHO-BAT cell line adapted to suspension growth in serum-free medium.

The genome-edited CHO host cell of the invention is preserved in China Center for Type Culture Collection (CCTCC NO: C2017127; date: Aug. 10, 2017; address: Wuhan University, Wuhan, China; classified designation: CHO-BAT-KF FUT8(−/−)).

DETAILED DESCRIPTION OF THE INVENTION

The technical scheme of the present invention is further described in combination with the detailed embodiments, which do not represent limitations to the protection scope of the present invention. Non-essential modifications and adjustments made by others according to the concept of the present invention shall still fall into the protection scope of the present invention.

It should be noted that in the present invention, "level" or "content" of the saccharide fraction of the antibody has the same meaning, indicating the mass ratio of a certain saccharide fraction in all saccharide fractions of the antibody.

According to the present invention, an "amino acid" refers to a carboxyl-α-amino acid, which may be encoded by a nucleic acid directly or in the form of precursor. A single amino acid is encoded by nucleic acid consisting of three nucleotides (so-called codons or base triple). Each amino acid is encoded by at least one codon. The encoding of the same amino acid by different codons is called "degeneracy of genetic code". The term "amino acid" used in the present application refers to the naturally occurring carboxyl-α-amino acid, which includes alanine (three-letter code: ala, one letter code: A), arginine (arg, R), asparagine (asn, N), asparagine (asn, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y) and valine (val, V).

In the present invention, the terms "polynucleotide" or "nucleic acid" or "nucleic acid sequence" are used interchangeably and refer to polymer molecules consisting of mononucleotide (also called bases) a, c, g, and t (or u in RNA), such as DNA, RNA, or modified forms thereof. The polynucleotide molecule may be a naturally occurring polynucleotide molecule, or a synthetic polynucleotide molecule, or a combination of one or more naturally occurring polynucleotide molecules and one or more synthetic polynucleotide molecules. The definition also includes naturally occurring polynucleotide molecules in which one or more nucleotides are altered (e.g., by mutagenesis), deleted, or added. The nucleic acids may be isolated or integrated into another nucleic acids such as expression cassettes, plasmids or chromosomes of the host cells. The nucleic acids are characterized by a nucleic acid sequence consisting of a mononucleotide. The operation and method for converting amino acid sequences such as polypeptides into corresponding nucleic acid sequences encoding the amino acid sequences are well known to those skilled in the art. Therefore, nucleic acids can be characterized by their nucleic acid sequences consisting of mononucleotide or by the amino acid sequences of the polypeptides encoded by them.

Also, the terms "polynucleotide" or "nucleic acid" or "nucleic acid sequence" may contain modified nucleotides in percentage of the total number of nucleotides present in the nucleic acid molecule, such as at least about 5%, 10%, 15%, 20%, 25%, 30%, 35%, 40%, 45%, 50%, 55%, 60%, 65%, 70%, 75%, 80%, 85%, 90%, 95% or 100% modified nucleotides.

The term "polypeptide" in the present invention is a polymer comprising amino acids linked by peptide bonds, which can be produced naturally or synthetically. Polypeptides with less than about 20 amino acid residues may be referred to as "peptides", however, molecules consisting of two or more peptides or molecules containing one polypeptide with more than 100 amino acid residues may be referred to as "proteins". Polypeptides may also contain non-amino acid components such as glycosyls, metal ions, or carboxylic acid esters. Non-amino acid components can be added by cells expressing this polypeptide and can vary with the type of cells. A polypeptide is defined herein according to its amino acid backbone structure or nucleic acid encoding it. The addition of glycosyl, for example, is generally not specified, but may be allowed. Also, the "polypeptide" may contain modified amino acids in percentage of the total number of amino acids present in the amino acid molecule, such as at least about 5%, 10%, 15%, 20%, 25%, 30%, 35%, 40%, 45%, 50%, 55%, 60%, 65%, 70%, 75%, 80%, 85%, 90%, 95% or 100% modified amino acids.

In the present invention, the term "host cell" refers to a microorganism or eukaryotic cell or cell line cultured in a mononuclear entity, which may be or has been used as a recipient of a recombinant vector or other transferred polynucleotide, and includes an offspring of the transfected original cell. In some embodiments, the host cells are non-lymphocytes, and the host cells produce the same unique glycan profile. In some embodiments, the host cells are, such as NS0 cells, simian COS cells, Chinese hamster ovary (CHO) cells, etc. In some embodiments, the host cells are selected from Chinese hamster ovary (CHO) cells. In some embodiments, the host cells are selected from CHO-K1, CHO-S, DUXB11, CHO-1E5, CHO3F, CHO/DG44, CHO-BAT and CHO-2.6 cells. In some embodiments, the host cells generate antibodies that exhibit a unique glycan profile. The genome-edited CHO host cells of the present invention, such as CHO-BAT-KF FUT8(–/–) can be grown in a culture and devices (including fermenters) that can be used to grow the culture. They can grow into a single layer or attach to a surface; alternatively, the host cells may grow in suspension. The cells can grow in serum-free medium. The medium may be a commercially available medium such as, but not limited to, DMEM/F12. The edited CHO host cells can maintain its specific unique glycan profile in the medium for many generations. For example, the edited CHO host cells retain their specific unique glycan profile for at least about 20, 30, 40 or 50 generations. In some embodiments, the modified CHO host cells retain their unique glycan profile for at least about 60 generations. In another embodiment, the modified CHO host cells retain their unique glycan profile for at least about 100, 150, 200, 500, 1000 or more generations.

The glycosylation mode of the host cells may be N- or O-glycosylation of any protein moiety, wherein one or more glucose molecules may be added to amide nitrogen of asparagine or hydroxyl oxygen of hydroxylysine, hydroxyproline, serine or threonine, respectively. The glycosylation mode is characterized by a change in the level of at least two or more glucose molecules or saccharides, such as monosaccharides, disaccharides, polysaccharides or oligosaccharides. For example, the glucose molecules may be trisaccharides, tetrasaccharides, pentoses, hexasaccharides, heptoses, octasaccharides, nonasaccharides, or derivatives thereof, such as deoxysaccharides (e.g., deoxyhexasaccharides); N- or O-substituted derivatives such as sialic acid; or saccharides with amino groups. The glucose molecules may include, but are not limited to, galactose (Gal), glucose (Glc), mannose (Man), N-acetylneuraminic acid (NeuAc), fucose (Fuc), N-acetylgalactosamine (GalNAc), N-acetylglucosamine (GlcNAc) and xylose. The glucose molecules can be linked to other glucose molecules by a or 13 linking.

The term "antibody" of the present invention includes all forms of antibodies, such as recombinant antibodies, humanized antibodies, chimeric antibodies, single chain antibodies, fusion antibodies, monoclonal antibodies and polyclonal antibodies. The antibodies may also be fragments. The antibodies can also bind drugs, toxins or therapeutic radioisotopes. The host cells of the present invention may also produce bispecific antibody fusion proteins, including hybrid antibodies that bind more than one antigen. Thus, antibodies include naked antibodies and binding antibodies as well as antibody fragments, and they may be single-specific or multi-specific.

As alternative embodiments, the antibodies or fragments thereof are not particularly limited to and may be selected from anti-HER2, anti-CD20, anti-EGF, anti-VEGF, anti-PDGF, anti-EpCam, anti-CD3, anti-CD4, anti-CD19, anti-CD30, anti-CD33, anti-CD40, anti-CD51, anti-CD55, anti-CD80, anti-CD95, anti-CCR2, anti-CCR3, anti-CCR4, anti-CCR5, anti-folic acids, anti-CXCR4, anti-EGFR or Trop2 antibodies, etc. As preferred embodiments, the antibodies are humanized or full human antibodies.

In a pharmaceutical composition of the present invention, a pharmaceutical preparation for storing the antibodies of the present invention is prepared in the form of a lyophilized preparation or an aqueous solution by mixing the antibodies with a desired degree of purity with optional physiologically acceptable carriers, excipients or stabilizers (Remington's Pharmaceutical Sciences 16th edition, Osol, A. Ed. (1980)). Acceptable carriers, excipients or stabilizers are non-toxic to the recipient at the dose and concentration applied, and include buffer solutions such as phosphates, citrates and other organic acids; antioxidants such as corbic acid and methionine; preservatives (such as benzyldimethyl octadecyl ammonium chloride; hexamethyl ammonium chloride; benzalkonium chloride, benzethonium chloride; phenol, butanol or benzyl alcohol; alkyl p-hydroxybenzoates, such as methyl or propyl p-hydroxybenzoate; catechol; resorcinol; cyclohexanol; 3-propanol and m-cresol); low molecular weight (less than about 10 residues) polypeptides; proteins such as serum albumin, gelatin, or immunoglobulin; hydrophilic polymers such as polyvinylpyrrolidone; amino acids such as glycine, glutamine, asparagine, histidine, arginine or lysine; monosaccharides, disaccharides and other carbohydrates such as glucose, mannose or dextrin; chelating agents such as EDTA; saccharides such as sucrose, mannitol, trehalose or sorbitol; salt-forming counter ions such as sodium; metal complexes (e.g. Zn-protein complexes); and/or nonionic surfactants such as Tween, Pluronics™ or polyethylene glycol (PEG).

The antibodies, pharmaceutical compositions and pharmaceutical preparations of the present invention may be administered by any suitable means, including parenteral, subcutaneous, intraperitoneal, intrapulmonary and intranasal means; and, if necessary, intralesional administration may be used for local immunosuppressive treatment. The parenteral perfusion includes intramuscular, intravenous, intraarterial, intraperitoneal or subcutaneous administrations. In addition, the antibody of the present invention can be suitably administered by pulsed perfusion (in particular, dose gradient changes of the antibodies of the present invention). Depending on the administration time, preferably, the injection administration is used; more preferably, intravenous or subcutaneous injection is used. ADCC (antibody-dependent cell-mediated cytotoxicity) refers to a cell-mediated reaction in which the effector cells expressing FCR (e.g., natural killer (NK) cells, neutrophils, and macrophages) recognize the antibodies bound to target cells and then lyse the target cells. Primary cells used to mediate ADCC include NK cells, monocytes and macrophages. In general, NK cells mainly express FcγRIII, while monocytes express FcγRI, FcγRII and FcγRIII. In the present invention, the maternal CHO cell line is edited to produce a CHO cell line with a unique glycan profile. The edited CHO cell line can then produce antibodies with higher ADCC activity than antibodies produced by the maternal CHO cells.

Example 1. Screening of Parent Cells Adapted to Serum-Free Suspension Culture

CHO-K1 was cultured in DMEM/F12 medium containing 10% FBS. When the cell confluence reached 80%-90%, washed with PBS and digest with trypsin. Then, terminated by DMEM/F12 medium containing 5% FBS, counted and centrifuged. Resuspended the cells in DMEM/F12 medium containing 5% FBS and seeded the cells at a density of $1 \times 10^5$ cells/ml. When the cell confluence reached 80%-90%, washed with PBS and digest with trypsin. Then, terminated by the DMEM/F12 medium containing 2% FBS, counted and centrifuged. Resuspended the cells in the DMEM/F12 medium containing 2% FBS and seeded at a density of $1 \times 10^5$ cells/ml. When the cell confluence reached 80%-90%, digested the cells with trypsin according to the previous steps, terminated by the DMEM/F12 medium containing 1% FBS, and carried out passage for 3-4 generations. Mixed the CD CHO medium with DMEM/F12 at a ratio of 1:1 (V/V), adjusted the final concentration to 6 mM glutamine, and adjusted the serum content to 1%. The CHO-K1 cells obtained above adapted to low serum culture were seeded into a T25 flask at a density of $3 \times 10^5$ cells/mL and were incubated in a 5% $CO_2$ incubator at 37° C. When the cell confluence reached 80-90%, digested the cells with trypsin and terminate by the mixed medium of DMEM/F12 containing 1% FBS and CD CHO medium (volume ratio 1:2), counted and centrifuged, seeded into a T25 flask at a density of $3 \times 10^5$ cells/ml, and incubated in a 5% $CO_2$ incubator at 37° C. Gradually reduced the ratio of DMEM/F12 in the mixture medium to (1:8) until the cell survival rate was more than 90%, which means that the DMEM/F12 component in the cell medium could be completely eliminated, and the CHO-K1 cell which adapted in chemical composition limitative CD CHO medium containing 1% serum was established. Then CHO-K1 was cultured in chemical composition limitative CD CHO medium containing 1% FBS. When cell confluence reached 80%-90%, washed with PBS and digested with trypsin. Then, terminated by the CD CHO medium containing 0.5% FBS, counted and centrifuged. Resuspended the cells in the CD CHO medium containing 0.5% FBS and seeded in a T25 flask at a density of $1 \times 10^5$ cells/ml. When the cell viability reached 80%-90%, washed the cells with PBS and digested with trypsin. Then, terminated by the CD CHO medium containing 0.25% FBS, counted and centrifuged. Resuspended the cells in the CD CHO medium containing 0.25% FBS and seeded at a density of $1 \times 10^5$ cells/ml. Until the cells grew healthily at this stage, started the next stage of decreasing serum concentration. After limiting dilution of CHO-K1 cells adapted to serum-free CD CHO culture, seeded into thirty 96-well plates, and adjusted the cell density to 1 cell/well. After two weeks, marked the monoclonal cells through microscopic examination. Transferred the clones with large cell area to a 24-well plate. After one week, marked the clones with high growth density and with consistent cell size through microscopic examination, and then transferred to a 6-well plate for further culture. After one week, clones that were completely suspended, less agglomerated, and had a denser cell density were marked through microscopic examination, and transferred each clone to a 100-ml triangular flask with a culture volume of 10 ml, respectively. Recorded the density and viability of each cell. CHO-K1 cells domesticated and adapted to serum-free culture were renamed CHO-BAT.

Example 2. Construction of FUT8 TALEN Recombinant Plasma

Figure 2:
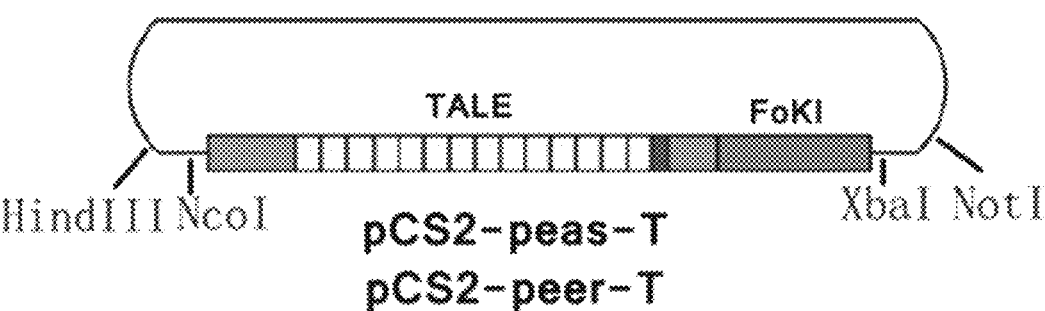
FIG. 2 shows a profile of TALEN expression plasmid pCS2-FokI.

The complete genome sequence (NW.003613860) of CHO-K1 of Chinese hamster ovarian cancer cells was analyzed to obtain the FUT8 genome sequence (Gene ID: 100751648) and its cDNA (see Table 1, SEQ ID NO. 8) sequence. The FUT8 genome consists of 9 exons and 11 introns. As the activity center of FUT8 enzyme is composed of amino acids (underlined amino acid sequence of SEQ ID NO. 9) encoded by exon 1 (SEQ ID NO. 7), the left and right flanks of exon 1 of FUT8 gene were designed as TALEN target sequences. FUT8 TALEN protein L130P (SEQ ID NO. 10) and R184P (SEQ ID NO. 11) were designed according to the TALEN design guidelines and the gene editing mechanism. L130P and FokI endonucleases formed a fusion protein L130-FokI (SEQ ID NO. 14), which recognized the left-wing base L130PTN (SEQ ID NO. 3) in exon 1, and the corresponding nucleic acid sequence L130-FokIN of the fusion protein L130-FokI is shown in SEQ ID NO. 15 with a length of 19 bp. R184P and FokI endonucleases formed a fusion protein R184-FokI (SEQ ID NO. 16), which recognized the right-wing base R184PTN (SEQ ID NO. 4) in exon 1, and the corresponding nucleic acid sequence R184P-FokIN of the fusion protein R184P-FokI is shown in SEQ ID NO. 17 with a length of 17 bp. The plasmid vector (see FIG. 2) containing TALEN protein encoding the left-wing L130PTN and the right-wing R184PTN of the exon 1 was constructed as described in Tomas Cermak et al. (2011). The restriction endonucleases NcoI and XbaI cleavage sites were added at both ends of L130-FokIN and R184P-FokIN. Synthesized these two sequences, and cloned them into pCS2-peas-T vector using NcoI and XbaI (FIG. 2). The left-wing binding sequence and the right-wing binding sequence had a gap sequence of 19 bp in length (Space, SEQ ID NO. 5). The DNA sequencing results of the two plasmids L130N and R184N of FUT8 TALEN are shown in Table 1, SEQ ID NO. 12 and SEQ NO. 13. The nucleic acid sequences such as L130N and R184N were translated into amino acids, and the amino acid sequences L130P and R184P of the corresponding sequences are shown in Table 1, SEQ ID NO. 10 and SEQ ID NO. 11.

TABLE 1

Sequence table

| L130for | gggtagctaattgtctttcag | SEQ ID NO. 1 |
| L130rev | taaatgccactgcttctata | SEQ ID NO. 2 |
| L130PTN | tccaagattcttgcaaagct | SEQ ID NO. 3 |
| R184PTN | aatgaagacttgaggaga | SEQ ID NO. 4 |
| Space | ggagcgcttaaaacaacaa | SEQ ID NO. 5 |

TABLE 1-continued

Sequence table

| PCR product | GGGTAGCTAATTGTCTTTCAGCCTCCTGGCCAAAGATACCATGAAAGTCAACT<br>TACGTTGTATTCTATATCTCAAACAACTCAGGGTGTTTCTTACTCTTTCCACA<br>GCATGTAGAGCCCAGGAAGCACAGGACAAGAAAGCTGCCTCCTTGTATCACCA<br>GGAAGATCTTTTTGTAAGAGTCATCACAGTATACCAGAGAGACTAATTTTGTC<br>TGAAGCATCATGTGTTGAAACAACAGAAACTTATTTTCCTGTGTGGCTAACTA<br>GAACCAGAGTACAATGTTTCCAATTCTTTGAGCTCCGAGAAGACAGAAGGGAG<br>TTGAAACTCTGAAAATGCGGGCATGGACTGGTTCCTGGCGTTGGATTATGCTC<br>ATTCTTTTTGCCTGGGGGGACCTTATTGTTTTATATAGGTGGTCATTTGGTTCG<br>AGATAATGACCACCCTGACCATTCTAGCAGAGAACTCTCCAAGATTCTTGCAA<br>AGCTGGAGCGCTTAAAACAACAAAATGAAGACTTGAGGAGAATGGCTGAGTCT<br>CTCCGGTAGGTTTGAAATACTCAAGGATTTGATGAAATACTGTGCTTGACCTT<br>TAGGTATAGGGTCTCAGTCTGCTGTTGAAAAATATAATTTCTACAAACCGTCT<br>TTGTAAAATTTTAAGTATTGTAGCAGACTTTTTAAAAGTCAGTGATACATCTA<br>TATAGTCAATATAGGTTTACATAGTTGCAATCTTATTTTGCATATGAATCAGT<br>ATATAGAAGCAGTGGCATTTA | SEQ ID<br>NO. 6 |
| Exon1 | ATGCGGGCATGGACTGGTTCCTGGCGTTGGATTATGCTCATTCTTTTTGCCTG<br>GGGGACCTTATTGTTTTATATAGGTGGTCATTTGGTTCGAGATAATGACCACC<br>CTGACCATTCTAGCAGAGAACTCTCCAAGATTCTTGCAAAGCTGGAGCGCTTA<br>AAACAACAAAATGAAGACTTGAGGAGAATGGCTGAGTCTCTCCGG | SEQ ID<br>NO. 7 |
| FUT8 cDNA | ATGCGGGCATGGACTGGTTCCTGGCGTTGGATTATGCTCATTCTTTTTGCCTG<br>GGGGACCTTATTGTTTTATATAGGTGGTCATTTGGTTCGAGATAATGACCACC<br>CTGACCATTCTAGCAGAGAACTCTCCAAGATTCTTGCAAAGCTGGAGCGCTTA<br>AAACAACAAAATGAAGACTTGAGGAGAATGGCTGAGTCTCTCCGAATACCAGA<br>AGGCCCTATTGATCAGGGGACAGCTACAGGAAGAGTCCGTGTTTTAGAAGAAC<br>AGCTTGTTAAGGCCAAAGAACAGATTGAAAATTACAAGAAACAAGCTAGGAAT<br>GATCTGGGAAAGGATCATGAAATCTTAAGGAGGAGGATTGAAAATGGAGCTAA<br>AGAGCTCTGGTTTTTTCTACAAAGTGAATTGAAGAAATTAAAGAAATTAGAAG<br>GAAACGAACTCCAAAGACATGCAGATGAAATTCTTTTGGATTTAGGACATCAT<br>GAAAGGTCTATCATGACAGATCTATACTACCTCAGTCAAACAGATGGAGCAGG<br>TGAGTGGCGGGAAAAAGAAGCCAAAGATCTGACAGAGCTGGTCCAGCGGAGAA<br>TAACATATCTGCAGAATCCCAAGGACTGCAGCAAAGCCAGAAAGCTGGTATGT<br>AATATCAACAAAGGCTGTGGCTATGGATGTCAACTCCATCATGTGGTTTACTG<br>CTTCATGATTGCTTATGGCACCCAGCGAACACTCATCTTGGAATCTCAGAATT<br>GGCGCTATGCTACTGGAGGATGGGAGACTGTGTTTAGACCTGTAAGTGAGACA<br>TGCACAGACAGGTCTGGCCTCTCCACTGGACACTGGTCAGGTGAAGTGAAGGA<br>CAAAAATGTTCAAGTGGTCGAGCTCCCCATTGTAGACAGCCTCCATCCTCGTC<br>CTCCTTACTTACCCTTGGCTGTACCAGAAGACCTTGCAGATCGACTCCTGAGA<br>GTCCATGGTGATCCTGCAGTGTGGTGGGTATCCCAGTTTGTCAAATACTTGAT<br>CCGTCCACAACCTTGGCTGGAAAGGGAAATAGAAGAAACCACCAAGAAGCTTG<br>GCTTCAAACATCCAGTTATTGGAGTCCATGTCAGACGCACTGACAAAGTGGGA<br>ACAGAAGCAGCCTTCCATCCCATTGAGGAATACATGGTACACGTTGAAGAACA<br>TTTTCAGCTTCTCGAACGCAGAATGAAAGTGGATAAAAAAAGAGTGTATCTGG<br>CCACTGATGACCCTTCTTTGTTAAAGGAGGCAAAGACAAAGTACTCCAATTAT<br>GAATTTATTAGTGATAACTCTATTTCTTGGTCAGCTGGACTACACAACCGATA<br>CACAGAAAATTCACTTCGGGGCGTGATCCTGGATATACACTTTCTCTCCCAGG<br>CTGACTTCCTTGTGTGTACTTTTTCATCCCAGGTCTGTAGGGTTGCTTATGAA<br>ATCATGCAAACACTGCATCCTGATGCCTCTGCAAACTTCCATTCTTTAGATGA<br>CATCTACTATTTTGGAGGCCAAAATGCCCACAACCAGATTGCAGTTTATCCTC<br>ACCAACCTCGAACTAAAGAGGAAATCCCCATGGAACCTGGAGATATCATTGGT<br>GTGGCTGGAAACCATTGGAATGGTTACTCTAAAGGTGTCAACAGAAACTAGG<br>AAAAACAGGCCTGTACCCTTCCTACAAAGTCCGAGAGAAGATAGAAACAGTCA<br>AATACCCTACATATCCTGAAGCTGAAAAATAG | SEQ ID<br>NO. 8 |
| FUT8 protein | <u>MRAWTGSWRWIMLILFAWGTLLFYIGGHLVRDNDHPDHSSRELSKILAKLERL</u><br><u>KQQNEDLRRMAESLRIPEGPIDQGTATGRVRVLEEQLVKAKEQIENYKKQARN</u><br>DLGKDHEILRRRIENGAKELWFFLQSELKKLKKLEGNELQRHADEILLDLGHH<br>ERSIMTDLYYLSQTDGAGEWREKEAKDLTELVQRRITYLQNPKDCSKARKLVC<br>NINKGCYGCQLHHVVYCFMIAYGTQRTLILESQNWRYATGGWETVFRPVSET<br>CTDRSGLSTGHWSGEVKDKNVQVVELPIVDSLHPRPPYLPLAVPEDLADRLLR<br>VHGDPAVWWVSQFVKYLIRPQPWLEREIEETTKKLGFKHPVIGVHVRRTDKVG<br>TEAAFHPIEEYMVHVEEHFQLLERRMKVDKKRVYLATDDPSLLKEAKTKYSNY<br>EFISDNSISWSAGLHNRYTENSLRGVILDIHFLSQADFLVCTFSSQVCRVAYE<br>IMQTLHPDASANFHSLDDIYYFGGQNAHNQIAVYPHQPRTKEEIPMEPGDIIG<br>VAGNHWNGYSKGVNRKLGKTGLYPSYKVREKIETVKYPTYPEAEK | SEQ ID<br>NO. 9 |
| L130P | LTPEQVVAIASHDGGKQALETVQRLLPVLCQAHGLTPAQVVAIASHDGGKQAL<br>ETVQRLLPVLCQAHGLTPAQVVAIASNIGGKQALETVQRLLPVLCQAHGLTPD<br>QVVAIASNIGGKQALETVQRLLPVLCQAHGLTPDQVVAIASNNGGKQALETVQ<br>RLLPVLCQAHGLTPDQVVAIASNIGGKQALETVQRLLPVLCQAHGLTPDQVVA<br>IASNGGGKQALETVQRLLPVLCQAHGLTPAQVVAIASNGGGKQALETVQRLLP<br>VLCQAHGLTPAQVVAIASHDGGKQALETVQRLLPVLCQAHGLTPAQVVAIASN<br>GGGKQALETVQRLLPVLCQAHGLTPAQVVAIASNGGGKQALETVQRLLPVLCQ<br>AHGLTPAQVVAIASNNGGKQALETVQRLLPVLCQAHGLTPDQVVAIASHDGGK<br>QALETVQRLLPVLCQAHGLTPAQVVAIASNIGGKQALETVQRLLPVLCQAHGL | SEQ ID<br>NO. 10 |

TABLE 1-continued

Sequence table

|  |  |  |
|---|---|---|
|  | TPDQVVAIASNIGGKQALETVQRLLPVLCQAHGLTPDQVVAIASNIGGKQALE<br>TVQRLLPVLCQAHGLTPDQVVAIASNNGGKQALETVQRLLPVLCQAHGLTPDQ<br>VVAIASHDGGKQALETVQRLLPVLCQAHGLTPAQVVAIASNGGGRPALESIVA<br>QLSRPDPALAAL |  |
| R184P | LTPEQVVAIASHDGGKQALETVQRLLPVLCQAHGLTPAQVVAIASNGGGKQAL<br>ETVQRLLPVLCQAHGLTPAQVVAIASHDGGKQALETVQRLLPVLCQAHGLTPA<br>QVVAIASHDGGKQALETVQRLLPVLCQAHGLTPAQVVAIASNGGGKQALETVQ<br>RLLPVLCQAHGLTPAQVVAIASHDGGKQALETVQRLLPVLCQAHGLTPAQVVA<br>IASNIGGKQALETVQRLLPVLCQAHGLTPDQVVAIASNIGGKQALETVQRLLP<br>VLCQAHGLTPDQVVAIASNNGGKQALETVQRLLPVLCQAHGLTPDQVVAIASN<br>GGGKQALETVQRLLPVLCQAHGLTPAQVVAIASHDGGKQALETVQRLLPVLCQ<br>AHGLTPAQVVAIASNGGGKQALETVQRLLPVLCQAHGLTPAQVVAIASNGGGK<br>QALETVQRLLPVLCQAHGLTPAQVVAIASHDGGKQALETVQRLLPVLCQAHGL<br>TPAQVVAIASNIGGKQALETVQRLLPVLCQAHGLTPDQVVAIASNGGGKQALE<br>TVQRLLPVLCQAHGLTPAQVVAIASNGGGRPALESIVAQLSRPDPALAAL | SEQ ID<br>NO. 11 |
| L130N | CTGACCCCGGAGCAGGTGGTGGCCATCGCTAGTCATGACGGTGGCAAACAGGC<br>TCTTGAGACCGTCCAACGCCTTCTACCAGTTCTCTGTCAAGCCCACGGACTAA<br>CCCCAGCGCAAGTTGTAGCGATTGCTAGTCATGACGGTGGCAAACAGGCTCTT<br>GAGACCGTCCAACGCCTTCTACCAGTTCTCTGTCAAGCCCACGGACTAACCCC<br>AGCGCAAGTTGTAGCGATTGCTAGTAATATTGGTGGCAAACAGGCACTTGAGA<br>CGGTTCAGCGCCTCCTTCCAGTTCTTTGTCAAGCTCACGGACTCACCCCAGAT<br>CAAGTTGTAGCGATTGCTAGTAATATTGGTGGCAAACAGGCACTTGAGACGGT<br>TCAGCGCCTCCTTCCAGTTCTTTGTCAAGCTCACGGACTCACCCCAGATCAAG<br>TTGTAGCGATTGCTAGTAACAATGGTGGCAAACAGGCTCTCGAAACCGTACAA<br>CGACTCCTCCCAGTTCTCTGTCAAGCCCACGGACTAACTCCTGATCAAGTTGT<br>AGCGATTGCTAGTAATATTGGTGGCAAACAGGCACTTGAGACGGTTCAGCGCC<br>TCCTTCCAGTTCTTTGTCAAGCTCACGGACTCACCCCAGATCAAGTTGTAGCG<br>ATTGCTAGTAATGGGGGTGGCAAACAGGCTCTTGAAACCGTGCAACGACTGCT<br>CCCAGTTCTCTGTCAAGCCCACGGCCTCACCCCGGCGCAAGTTGTAGCGATTG<br>CTAGTAATGGGGGTGGCAAACAGGCTCTTGAAACCGTGCAACGACTGCTCCCA<br>GTTCTCTGTCAAGCCCACGGCCTCACCCCGGCGCAAGTTGTAGCGATTGCTAG<br>TCATGACGGTGGCAAACAGGCTCTTGAGACCGTCCAACGCCTTCTACCAGTTC<br>TCTGTCAAGCCCACGGACTAACCCCAGCGCAAGTTGTAGCGATTGCTAGTAAT<br>GGGGGTGGCAAACAGGCTCTTGAAACCGTGCAACGACTGCTCCCAGTTCTCTG<br>TCAAGCCCACGGCCTCACCCCGGCGCAAGTTGTAGCGATTGCTAGTAATGGGG<br>GTGGCAAACAGGCTCTTGAAACCGTGCAACGACTGCTCCCAGTTCTCTGTCAA<br>GCCCACGGCCTCACCCCGGCGCAAGTTGTAGCGATTGCTAGTAACAATGGTGG<br>CAAACAGGCTCTCGAAACCGTACAACGACTCCTCCCAGTTCTCTGTCAAGCCC<br>ACGGACTAACTCCTGATCAAGTTGTAGCGATTGCTAGTCATGACGGTGGCAAA<br>CAGGCTCTTGAGACCGTCCAACGCCTTCTACCAGTTCTCTGTCAAGCCCACGG<br>ACTAACCCCAGCGCAAGTTGTAGCGATTGCTAGTAATATTGGTGGCAAACAGG<br>CACTTGAGACGGTTCAGCGCCTCCTTCCAGTTCTTTGTCAAGCTCACGGACTC<br>ACCCCAGATCAAGTTGTAGCGATTGCTAGTAATATTGGTGGCAAACAGGCACT<br>TGAGACGGTTCAGCGCCTCCTTCCAGTTCTTTGTCAAGCTCACGGACTCACCC<br>CAGATCAAGTTGTAGCGATTGCTAGTAACAATGGTGGCAAACAGGCTCTCGAA<br>ACCGTACAACGACTCCTCCCAGTTCTCTGTCAAGCCCACGGACTAACTCCTGA<br>TCAAGTTGTAGCGATTGCTAGTCATGACGGTGGCAAACAGGCTCTTGAGACCG<br>TCCAACGCCTTCTACCAGTTCTCTGTCAAGCCCACGGACTAACCCCAGCGAAGTTG<br>TAGCGATTGCTAGTAATGGCGGCGGTCGACCGGCGCTGGAGAGCATTGTTGCC<br>CAGTTATCTCGCCCTGATCCGGCGTTGGCCGCGTTG | SEQ ID<br>NO. 12 |
| R184N | CTGACCCCGGAGCAGGTGGTGGCCATCGCTAGTCATGACGGTGGCAAACAGGC<br>TCTTGAGACCGTCCAACGCCTTCTACCAGTTCTCTGTCAAGCCCACGGACTAA<br>CCCCAGCGCAAGTTGTAGCGATTGCTAGTAATGGGGGTGGCAAACAGGCTCTT<br>GAAACCGTGCAACGACTGCTCCCAGTTCTCTGTCAAGCCCACGGCCTCACCCC<br>GGCGCAAGTTGTAGCGATTGCTAGTCATGACGGTGGCAAACAGGCTCTTGAGA<br>CCGTCCAACGCCTTCTACCAGTTCTCTGTCAAGCCCACGGACTAACCCCAGCGCAAG<br>CAAGTTGTAGCGATTGCTAGTCATGACGGTGGCAAACAGGCTCTTGAGACCGT<br>CCAACGCCTTCTACCAGTTCTCTGTCAAGCCCACGGACTAACCCCAGCGCAAG<br>TTGTAGCGATTGCTAGTAATGGGGGTGGCAAACAGGCTCTTGAAACCGTGCAA<br>CGACTGCTCCCAGTTCTCTGTCAAGCCCACGGCCTCACCCCGGCGCAAGTTGT<br>AGCGATTGCTAGTCATGACGGTGGCAAACAGGCTCTTGAGACCGTCCAACGCC<br>TTCTACCAGTTCTCTGTCAAGCCCACGGACTAACCCCAGCGCAAGTTGTAGCG<br>ATTGCTAGTAATATTGGTGGCAAACAGGCACTTGAGACGGTTCAGCGCCTCCT<br>TCCAGTTCTTTGTCAAGCTCACGGACTCACCCCAGATCAAGTTGTAGCGATTG<br>CTAGTAATATTGGTGGCAAACAGGCACTTGAGACGGTTCAGCGCCTCCTTCCA<br>GTTCTTTGTCAAGCTCACGGACTCACCCCAGATCAAGTTGTAGCGATTGCTAG<br>TAACAATGGTGGCAAACAGGCTCTCGAAACCGTACAACGACTCCTCCCAGTTC<br>TCTGTCAAGCCCACGGACTAACTCCTGATCAAGTTGTAGCGATTGCTAGTAAT<br>GGGGGTGGCAAACAGGCTCTTGAAACCGTGCAACGACTGCTCCCAGTTCTCTG<br>TCAAGCCCACGGCCTCACCCCGGCGCAAGTTGTAGCGATTGCTAGTCATGACG<br>GTGGCAAACAGGCTCTTGAGACCGTCCAACGCCTTCTACCAGTTCTCTGTCAA<br>GCCCACGGACTAACCCCAGCGCAAGTTGTAGCGATTGCTAGTAATGGGGGTGG<br>CAAACAGGCTCTTGAAACCGTGCAACGACTGCTCCCAGTTCTCTGTCAAGCCC | SEQ ID<br>NO. 13 |

TABLE 1-continued

Sequence table

```
ACGGCCTCACCCCGGCGCAAGTTGTAGCGATTGCTAGTAATGGGGGTGGCAAA
CAGGCTCTTGAAACCGTGCAACGACTGCTCCCAGTTCTCTGTCAAGCCCACGG
CCTCACCCCGGCGCAAGTTGTAGCGATTGCTAGTCATGACGGTGGCAAACAGG
CTCTTGAGACCGTCCAACGCCTTCTACCAGTTCTCTGTCAAGCCCACGGACTA
ACCCCAGCGCAAGTTGTAGCGATTGCTAGTAATATTGGTGGCAAACAGGCACT
TGAGACGGTTCAGCGCCTCCTTCCAGTTCTTTGTCAAGCTCACGGACTCACCC
CAGATCAAGTTGTAGCGATTGCTAGTAATGGGGGTGGCAAACAGGCTCTTGAA
ACCGTGCAACGACTGCTCCCAGTTCTCTGTCAAGCCCACGGCCTCACCCCGGC
GCAAGTTGTAGCGATTGCTAGTAATGGCGGCGGTCGACCGGCGCTGGAGAGCA
TTGTTGCCCAGTTATCTCGCCCTGATCCGGCGTTGGCCGCGTTG
```

| L130P-<br>FokI | MAPKKKRKVYPYDVPDYAGYPYDVPDYAGSYPYDVPDYAAHGTVDLRTLGYSQ<br>QQQEKIKPKVRSTVAQHHEALVGHGFTHAHIVALSQHPAALGTVAVKYQDMIA<br>ALPEATHEAIVGVGKQWSGARALEALLTVAGELRGPPLQLDTGQLLKIAKRGG<br>VTAVEAVHAWRNALTGAPLNLTPEQVVAIASHDGGKQALETVQRLLPVLCQAH<br>GLTPAQVVAIASHDGGKQALETVQRLLPVLCQAHGLTPAQVVAIASNIGGKQA<br>LETVQRLLPVLCQAHGLTPDQVVAIASNIGGKQALETVQRLLPVLCQAHGLTP<br>DQVVAIASNNGGKQALETVQRLLPVLCQAHGLTPDQVVAIASNIGGKQALETV<br>QRLLPVLCQAHGLTPDQVVAIASNGGGKQALETVQRLLPVLCQAHGLTPAQVV<br>AIASNGGGKQALETVQRLLPVLCQAHGLTPAQVVAIASHDGGKQALETVQRLL<br>PVLCQAHGLTPAQVVAIASNGGGKQALETVQRLLPVLCQAHGLTPAQVVAIAS<br>NGGGKQALETVQRLLPVLCQAHGLTPAQVVAIASNNGGKQALETVQRLLPVLC<br>QAHGLTPDQVVAIASHDGGKQALETVQRLLPVLCQAHGLTPAQVVAIASNIGG<br>KQALETVQRLLPVLCQAHGLTPDQVVAIASNIGGKQALETVQRLLPVLCQAHG<br>LTPDQVVAIASNIGGKQALETVQRLLPVLCQAHGLTPDQVVAIASNNGGKQAL<br>ETVQRLLPVLCQAHGLTPDQVVAIASHDGGKQALETVQRLLPVLCQAHGLTPA<br>QVVAIASNGGGRPALESIVAQLSRPDPALAALTNDHLVALACLGGRPALDAVK<br>KGLPHAPALIKRTNRRIPERTSHRVAGSQLVKSELEEKKSELRHKLKYVPHEY<br>IELIEIARNPTQDRILEMKVMEFFMKVYGYRGEHLGGSRKPDGAIYTVGSPID<br>YGVIVDTKAYSGGYNLPIGQAREMQRYVEENQTRNKHINPNEWWKVYPSSVTE<br>FKFLFVSGHFKGNYKAQLTRLNHITNCNGAVLSVEELLIGGEMIKAGTLTLEE<br>VRRKFNNGEINF* | SEQ ID<br>NO. 14 |
| L130P-<br>FokIN | atggctccaaagaagaagcgtaaggtatacccatacgatgttcctgactatgc<br>gggctatccctatgacgtcccggactatgcaggatcgtatccatatgacgttc<br>cagattacgctgctcatggtaccgtggatctacgcacgctcggctacagccag<br>cagcaacaggagaagatcaaaccgaaggttcgttcgacagtggcgcagcacca<br>cgaggcactggtcggccacgggtttacacacgcgcacatcgttgcgctcagcc<br>aacacccggcagcgttagggaccgtcgctgtcaagtatcaggacatgatcgca<br>gcgttgccagaggcgacacacgaagcgatcgttggcgtcggcaaacagtggtc<br>cggcgcacgcgctctggaggccttgctcacggtggcgggagagttgagaggtc<br>caccgttacagttggacacaggccaacttctcaagattgcaaaacgtggcggc<br>gtgaccgcagtggaggcagtgcatgcatggcgcaatgcactgacgggtgcccc<br>cctgaacctgaccccgggagcaggtggtggccatcgcTAGTCATGACGGTGGCA<br>AACAGGCTCTTGAGACCGTCCAACGCCTTCTACCAGTTCTCTGTCAAGCCCAC<br>GGACTAACCCCAGCGCAAGTTGTAGCGATTGCTAGTCATGACGGTGGCAAACA<br>GGCTCTTGAGACCGTCCAACGCCTTCTACCAGTTCTCTGTCAAGCCCACGGAC<br>TAACCCCAGCGCAAGTTGTAGCGATTGCTAGTAATATTGGTGGCAAACAGGCA<br>CTTGAGACGGTTCAGCGCCTCCTTCCAGTTCTTTGTCAAGCTCACGGACTCAC<br>CCCAGATCAAGTTGTAGCGATTGCTAGTAATATTGGTGGCAAACAGGCACTTG<br>AGACGGTTCAGCGCCTCCTTCCAGTTCTTTGTCAAGCTCACGGACTCACCCCA<br>GATCAAGTTGTAGCGATTGCTAGTAACAATGGTGGCAAACAGGCTCTCGAAAC<br>CGTACAACGACTCCTCCCAGTTCTCTGTCAAGCCCACGGACTAACTCCTGATC<br>AAGTTGTAGCGATTGCTAGTAATATTGGTGGCAAACAGGCACTTGAGACGGTT<br>CAGCGCCTCCTTCCAGTTCTTTGTCAAGCTCACGGACTCACCCCAGATCAAGT<br>TGTAGCGATTGCTAGTAATGGGGGTGGCAAACAGGCTCTTGAAACCGTGCAAC<br>GACTGCTCCCAGTTCTCTGTCAAGCCCACGGCCTCACCCCGGCGCAAGTTGTA<br>GCGATTGCTAGTAATGGGGGTGGCAAACAGGCTCTTGAAACCGTGCAACGACT<br>GCTCCCAGTTCTCTGTCAAGCCCACGGCCTCACCCCGGCGCAAGTTGTAGCGA<br>TTGCTAGTCATGACGGTGGCAAACAGGCTCTTGAGACCGTCCAACGCCTTCTA<br>CCAGTTCTCTGTCAAGCCCACGGACTAACCCCAGCGCAAGTTGTAGCGATTGC<br>TAGTAATGGGGGTGGCAAACAGGCTCTTGAAACCGTGCAACGACTGCTCCCAG<br>TTCTCTGTCAAGCCCACGGCCTCACCCCGGCGCAAGTTGTAGCGATTGCTAGT<br>AATGGGGGTGGCAAACAGGCTCTTGAAACCGTGCAACGACTGCTCCCAGTTCT<br>CTGTCAAGCCCACGGCCTCACCCCGGCGCAAGTTGTAGCGATTGCTAGTAACA<br>ATGGTGGCAAACAGGCTCTCGAAACCGTACAACGACTCCTCCCAGTTCTCTGT<br>CAAGCCCACGGACTAACTCCTGATCAAGTTGTAGCGATTGCTAGTCATGACGG<br>TGGCAAACAGGCTCTTGAGACCGTCCAACGCCTTCTACCAGTTCTCTGTCAAG<br>CCCACGGACTAACCCCAGCGCAAGTTGTAGCGATTGCTAGTAATATTGGTGGC<br>AAACAGGCACTTGAGACGGTTCAGCGCCTCCTTCCAGTTCTTTGTCAAGCTCA<br>CGGACTCACCCCAGATCAAGTTGTAGCGATTGCTAGTAATATTGGTGGCAAAC<br>AGGCACTTGAGACGGTTCAGCGCCTCCTTCCAGTTCTTTGTCAAGCTCACGGA<br>CTCACCCCAGATCAAGTTGTAGCGATTGCTAGTAATGGGGGTGGCAAACAGGC<br>ACTTGAGACGGTTCAGCGCCTCCTTCCAGTTCTTTGTCAAGCTCACGGACTCA<br>CCCCAGATCAAGTTGTAGCGATTGCTAGTAACAATGGTGGCAAACAGGCTCTC<br>GAAACCGTACAACGACTCCTCCCAGTTCTCTGTCAAGCCCACGGACTAACTCC<br>TGATCAAGTTGTAGCGATTGCTAGTCATGACGGTGGCAAACAGGCTCTTGAGA<br>CCGTCCAACGCCTTCTACCAGTTCTCTGTCAAGCCCACGGACTAACCCCAGCG | SEQ ID<br>NO. 15 |

TABLE 1-continued

Sequence table

```
              CAAGTTGTAGCGATTGCTAGTAATGGCggcggtcgaccggcgctggagagcat
              tgttgcccagttatctcgccctgatccggcgttggccgcgttgaccaacgacc
              acctcgtcgccttggcctgcctcggcggacgtcctgcgctggatgcagtgaaa
              aagggattgccgcacgcgccggccttgatcaaaagaaccaatcgccgtattcc
              cgaacgcacatccatcgcgttgccggatcccaactagtcaaaagtgaactgg
              aggagaagaaatctgaacttcgtcataaaattgaaatatgtgcctcatgaatat
              attgaattaattgaaattgccagaaatcccactcaggatagaattcttgaaat
              gaaggtaatggaatttttttatgaaagtttatggatatagaggtgagcatttgg
              gtggatcaaggaaaccggacggagcaatttatactgtcggatctcctattgat
              tacggtgtgatcgtggatactaaggcttatagcggaggttataatctgccaat
              tggccaagcacgagaaatgcaacgatatgtcgaagaaaatcaaacacgaaaca
              aacatatcaaccctaatgaatggtggaaagtctatccatcttctgtaacggaa
              tttaagtttttatttgtgagtggtcactttaaaggaaactacaaagctcagct
              tacacggattaaatcatatcactaattgtaatggagctgttcttagtgtagaag
              agctttttaattggtggagaaatgattaaagccggcacattaaccttagaggaa
              gtgagacggaaatttaataacggcgagataaacttt R184P-       MAPKKKRKVYPYDVPDYAGYPYDVPDYAGSYPYDVPDYAAHGTVDLRTLGYSQ         SEQ ID
FokI         QQQEKIKPKVRSTVAQHHEALVGHGFTHAHIVALSQHPAALGTVAVKYQDMIA         NO. 16
              ALPEATHEAIVGVGKQWSGARALEALLTVAGELRGPPLQLDTGQLLKIAKRGG
              VTAVEAVHAWRNALTGAPLNLTPEQVVAIASHDGGKQALETVQRLLPVLCQAH
              GLTPAQVVAIASNGGGKQALETVQRLLPVLCQAHGLTPAQVVAIASHDGGKQA
              LETVQRLLPVLCQAHGLTPAQVVAIASHDGGKQALETVQRLLPVLCQAHGLTP
              AQVVAIASNGGGKQALETVQRLLPVLCQAHGLTPAQVVAIASHDGGKQALETV
              QRLLPVLCQAHGLTPAQVVAIASNIGGKQALETVQRLLPVLCQAHGLTPDQVV
              AIASNIGGKQALETVQRLLPVLCQAHGLTPDQVVAIASNNGGKQALETVQRLL
              PVLCQAHGLTPDQVVAIASNGGGKQALETVQRLLPVLCQAHGLTPAQVVAIAS
              HDGGKQALETVQRLLPVLCQAHGLTPAQVVAIASNGGGKQALETVQRLLPVLC
              QAHGLTPAQVVAIASNGGGKQALETVQRLLPVLCQAHGLTPAQVVAIASHDGG
              KQALETVQRLLPVLCQAHGLTPAQVVAIASNIGGKQALETVQRLLPVLCQAHG
              LTPDQVVAIASNGGGKQALETVQRLLPVLCQAHGLTPAQVVAIASNGGGRPAL
              ESIVAQLSRPDPALAALTNDHLVALACLGGRPALDAVKKGLPHAPALIKRTNR
              RIPERTSHRVAGSQLVKSELEEKKSELRHKLKYVPHEYIELIEIARNPTQDRI
              LEMKVMEFFMKVYGYRGEHLGGSRKPDGAIYTVGSPIDYGVIVDTKAYSGGYN
              LPIGQADAMQSYVEENQTRNKHINPNEWWKVYPSSVTEFKFLFVSGHFKGNYK
              AQLTRLNHITNCNGAVLSVEELLIGGEMIKAGTLTLEEVRRKFNNGEINF*

R184P-       cgccattctgcctggggacgtcggagcaagcttgatttaggtgacactataga         SEQ ID
FokIN        atacaagctacttgttcttttgcaggatctgccaccatggctccaaagaaga         NO. 17
              agcgtaaggtatacccatacgatgttcctgactatgcgggctatccctatgac
              gtcccggactatgcaggatcgtatccatatgacgttccagattacgctgctca
              tggtaccgtggatctacgcacgctcggctacagccagcagcaacaggagaaga
              tcaaaccgaaggttcgttcgacagtggcgcagcaccacgaggcactggtcggc
              cacgggtttacacacgcgcacatcgttgcgctcagccaacacccggcagcgtt
              agggaccgtcgctgtcaagtatcaggacatgatcgcagcgttgccagaggcga
              cacacgaagcgatcgttggcgtcggcaaacagtggtccggcgcacgcgctctg
              gaggccttgctcacggtggcgggagagttgagaggtccaccgttacagttgga
              cacaggccaacttctcaagattgcaaaacgtggcggcgttgaccgcagtggagg
              cagtgcatgcatggcgcaatgcactgacgggtgccccctgaacctgaccccg
              gagcaggtggtggccatcgcTAGTCATGACGGTGGCAAACAGGCTCTTGAGAC
              CGTCCAACGCCTTCTACCAGTTCTCTGTCAAGCCCACGGACTAACCCCAGCGC
              AAGTTGTAGCGATTGCTAGTAATGGGGGGTGGCAAACAGGCTCTTGAAACCGTG
              CAACGACTGCTCCCAGTTCTCTGTCAAGCCCACGGCCTCACCCCGGCGCAAGT
              TGTAGCGATTGCTAGTCATGACGGTGGCAAACAGGCTCTTGAGACCGTCCAAC
              GCCTTCTACCAGTTCTCTGTCAAGCCCACGGACTAACCCCAGCGCAAGTTGTA
              GCGATTGCTAGTCATGACGGTGGCAAACAGGCTCTTGAGACCGTCCAACGCCT
              TCTACCAGTTCTCTGTCAAGCCCACGGACTAACCCCAGCGCAAGTTGTAGCGA
              TTGCTAGTAATGGGGGGTGGCAAACAGGCTCTTGAAACCGTGCAACGACTGCTC
              CCAGTTCTCTGTCAAGCCCACGGCCTCACCCCGGCGCAAGTTGTAGCGATTGC
              TAGTCATGACGGTGGCAAACAGGCTCTTGAGACCGTCCAACGCCTTCTACCAG
              TTCTCTGTCAAGCCCACGGACTAACCCCAGCGCAAGTTGTAGCGATTGCTAGT
              AATATTGGTGGCAAACAGGCACTTGAGACGGTTCAGCGCCTCCTTCCAGTTCT
              TTGTCAAGCTCACGGACTCACCCCAGATCAAGTTGTAGCGATTGCTAGTAATA
              TTGGTGGCAAACAGGCACTTGAGACGGTTCAGCGCCTCCTTCCAGTTCTTTGT
              CAAGCTCACGGACTCACCCCAGATCAAGTTGTAGCGATTGCTAGTAACAATGG
              TGGCAAACAGGCTCTCGAAACCGTACAACGACTCCTCCCAGTTCTCTGTCAAG
              CCCACGGACTAACTCCTGATCAAGTTGTAGCGATTGCTAGTAATGGGGGGTGGC
              AAACAGGCTCTTGAAACCGTGCAACGACTGCTCCCAGTTCTCTGTCAAGCCCA
              CGGCCTCACCCCGGCGCAAGTTGTAGCGATTGCTAGTCATGACGGTGGCAAAC
              AGGCTCTTGAGACCGTCCAACGCCTTCTACCAGTTCTCTGTCAAGCCCACGGA
              CTAACCCCAGCGCAAGTTGTAGCGATTGCTAGTAATGGGGGGTGGCAAACAGGC
              TCTTGAAACCGTGCAACGACTGCTCCCAGTTCTCTGTCAAGCCCACGGCCTCA
              CCCCGGCGCAAGTTGTAGCGATTGCTAGTAATGGGGGGTGGCAAACAGGCTCTT
              GAAACCGTGCAACGACTGCTCCCAGTTCTCTGTCAAGCCCACGGCCTCACCCC
              GGCGCAAGTTGTAGCGATTGCTAGTCATGACGGTGGCAAACAGGCTCTTGAGA
              CCGTCCAACGCCTTCTACCAGTTCTCTGTCAAGCCCACGGACTAACCCCAGCG
              CAAGTTGTAGCGATTGCTAGTAATATTGGTGGCAAACAGGCACTTGAGACGGT
              TCAGCGCCTCCTTCCAGTTCTTTGTCAAGCTCACGGACTCACCCCAGATCAAG
```

TABLE 1-continued

Sequence table

```
TTGTAGCGATTGCTAGTAATGGGGGTGGCAAACAGGCTCTTGAAACCGTGCAA
CGACTGCTCCCAGTTCTCTGTCAAGCCCACGGCCTCACCCCGGCGCAAGTTGT
AGCGATTGCTAGTAATGGCggcggtcgaccggcgctggagagcattgttgccc
agttatctcgccctgatccggcgttggccgcgttgaccaacgaccacctcgtc
gccttggcctgcctcggcggacgtcctgcgctggatgcagtgaaaaagggatt
gccgcacgcgccggccttgatcaaaagaaccaatcgccgtattcccgaacgca
catcccatcgcgttgccggatcccaactagtcaaaagtgaactggaggagaag
aaatctgaacttcgtcataaattgaaatatgtgcctcatgaatatattgaatt
aattgaaattgccagaaatcccactcaggatagaattcttgaaatgaaggtaa
tggaatttttttatgaaagtttatggatatagaggtgagcatttgggtggatca
aggaaaccggacggagcaatttatactgtcggatctcctattgattacggtgt
gatcgtggatactaaagcttatagcggaggttataatctgccaattggccaag
cagatgccatgcaaagctatgtcgaagaaatcaaacacgaaacaaacatatc
aaccctaatgaatggtggaaagtctatccatcttctgtaacggaatttaagtt
tttatttgtgagtggtcactttaaaggaaactacaaagctcagcttacacgat
taaatcatatcactaattgtaatggagctgttcttagtgtagaagagctttta
attggtggagaaatgattaaagccggcacattaaccttagaggaagtgagacg
gaaatttaataacggcgagataaacttttaatctagaactatagtgagtcgta
ttacgtagatccagacatgataagatacattgatgagtttggacaaaccacaa
ctagaatgcagtgaaaaaaatgctttatttgtgaaatttgtgatgctattgct
ttatttgtaaccattataagctgcaataaacaagttaacaacaacaattgcat
tcattttatgtttcaggttcaggggggaggtgtgggaggtttttttaattcgcgg
ccgcggcgccaatgcattgggcccggtacgtacccagcttttgttcccttag
tgagggttaattgcgcgcttggcgtaatcatggtcatagctgtttcctgtgtg
aaattgttatccgctcacaattccacacaacatacgagccggaagcataaagt
gtaaagcctggggtgcctaatgagtgagctaactcacattaattgcgttgcgc
tcactgcccgctttccagtcgggaaacctgtcgtgccagctgcattaatgaat
cggccaacgcgcggggagaggcggtttgcgtattgggcgctcttccgcttcct
cgctcactgactcgctgcgctcggtcgttcggctgcggcgagcggtatcagct
cactcaaaggcggtaatacggttatccacagaatcaggggataacgcaggaaa
gaacatgtgagcaaaaggccagcaaaaggccaggaaccgtaaaaaggccgcgt
tgctggcgtttttccataggctccgcccccctgacgagcatcacaaaaatcga
cgctcaagtcagaggtggcgaaacccgacaggactataaagataccaggcgtt
tccccctggaagctccctcgtgcgctctcctgttccgaccctgccgcttaccg
gatacctgtccgcctttctcccttcgggaagcgtggcgctttctcatagctca
cgctgtaggtatctcagttcggtgtaggtcgttcgctccaagctgggctgtgt
gcacgaacccccgttcagcccgaccgctgcgccttatccggtaactatcgtc
ttgagtccaacccggtaagacacgacttatcgccactggcagcagccactggt
aacaggattagcagagcgaggtatgtaggcggtgctacagagttcttgaagtg
gtggcctaactacggctacactagaaggacagtatttggtatctgcgctctgc
tgaagccagttaccttcggaaaaagagttggtagctcttgatccggcaaacaa
accaccgctggtagcggtggtttttttgtttgcaagcagcagattacgcgcag
aaaaaaaggatctcaagaagatcctttgatcttttctacggggtctgacgctc
agtggaacgaaaactcacgttaagggattttggtcatgagattatcaaaaagg
atcttcacctagatccttttaaattaaaaatgaagttttaaatcaatctaaag
tatatatgagtaaacttggtctgacagttaccaatgcttaatcagtgaggcac
ctatctcagcgatctgtctatttcgttcatccatagttgcctgactccccgtc
gtgtagataactacgatacgggagggcttaccatctggccccagtgctgcaat
gataccgcgagacccacgctcaccggctccagatttatcagcaataaaccagc
cagccggaagggccgagcgcagaagtggtcctgcaactttatccgcctccatc
cagtctattaattgttgccgggaagctagagtaagtagttcgccagttaatag
tttgcgcaacgttgttgccattgctacaggcatcgtggtgtcacgctcgtcgt
ttggtatggcttcattcagctccggttcccaacgatcaaggcgagttacatga
tcccccatgttgtgcaaaaaagcggttagctccttcggtcctccgatcgttgt
cagaagtaagttggccgcagtgttatcactcatggttatggcagcactgcata
attctcttactgtcatgccatccgtaagatgcttttctgtgactggtgagtac
tcaaccaagtcattctgagaatagtgtatgcggcgaccgagttgctcttgccc
ggcgtcaatacgggataataccgcgccacatagcagaactttaaaagtgctca
tcattggaaaacgttcttcggggcgaaaactctcaaggatcttaccgctgttg
agatccagttcgatgtaacccactcgtgcacccaactgatcttcagcatcttt
tactttcaccagcgtttctgggtgagcaaaaacaggaaggcaaaatgccgcaa
aaaagggaataagggcgcacggaaatgttgaatactcatactcttcctttttt
caatattattgaagcatttatcagggttattgtctcatgagcggatacatatt
tgaatgtatttagaaaaataaacaaatagggggttccgcgcacatttccccgaa
aagtgccacctaaattgtaagcgttaatattttgttaaaattcgcgttaaatt
tttgttaaatcagctcattttttaaccaataggccgaaatcggcaaaatccct
tataaatcaaaagaatagaccgagatagggttgagtgttgttccagtttggaa
caagagtccactattaaagaacgtggactccaacgtcaaagggcgaaaaaccg
tctatcagggcgatggcccactacgtgaaccatcaccctaatcaagtttttttg
gggtcgaggtgccgtaaagcactaaatcggaacctaaagggagccccgatt
tagagcttgacggggaaagccggcgaacgtggcgagaaaggaagggaagaaag
cgaaaggagcgggcgctagggcgctggcaagtgtagcggtcacgctgcgcgta
accaccacacccgccgcgcttaatgcgccgctacagggcgcgtccccattcgcc
attcaggctgcgcaactgttgggaagggcgatcggtgcgggcctcttcgctat
tacgccagtcgattatatactcgagatatatttcgaccatagccaattcaata
tggcgtatatggactcatgccaattcaatatggtggatctggacctgtgccaa
ttcaatatggcgtatatggactcgtgccaattcaatatggtggatctggaccc
cagccaattcaatatggcggacttggcaccatgccaattcaatatggcggact
```

TABLE 1-continued

Sequence table

```
tggcactgtgccaactggggagggtctacttggcacggtgccaagtttgagg
aggggtcttggccctgtgccaagtccgccatattgaattggcatggtgccaat
aatggcggccatattggctatatgccaggatcaatatataggcaatatccaat
atggccctatgccaatatggctattggcaggttcaatactatgtattggccc
tatgccatatagtattccatatatggggtttcctattgacgtagatagcccct
cccaatgggcggtcccatataccatatatgggggcttcctaataccgcccatag
ccactcccccattgacgtcaatggtctctatatatggtctttcctattgacgt
catatgggcggtcctattgacgtatatggcgcctccccccattgacgtcaatta
cggtaaatggcccgcctggctcaatgcccattgacgtcaataggaccacccac
cattgacgtcaatgggatggctcattgcccattcatatccgttctcacgcccc
ctattgacgtcaatgacggtaaatggcccacttggcagtacatcaatatctat
taatagtaacttggcaagtacattactattggaaggacgccagggtacattgg
cagtactcccattgacgtcaatggcggtaaatggcccgcgatggctgccaagt
acatccccattgacgtcaatgggagggcaatgacgcaaatgggcgttccat
tgacgtaaatgggcggtaggcgtgcctaatgggaggtctatataagcaatgct
cgtttagggaac
```

BAT1206F  QIVLSQSPAILSASPGEKVTMTCRASSSVSYIHWFQQKPGSSPKPWIYATSNL      SEQ ID
light     ASGVPVRFSGSGSGTSYSLTISRVEAEDAATYYCQQWTSNPPTFGGGTKLEIK    NO. 18
chain     RTVAAPSVFIFPPSDEQLKSGTASVVCLLNNFYPREAKVQWKVDNALQSGNSQ
          ESVTEQDSKDSTYSLSSTLTLSKADYEKHKVYACEVTHQGLSSPVTKSFNRGE
          C BAT1206F  QVQLQQPGAELVKPGASVKMSCKASGYTFTSYNMHWVKQTPGRGLEWIGAIYP      SEQ ID
heavy     GNGDTSYNQKFKGKATLTADKSSSTAYMQLSSLTSEDSAVYYCARSTYYGGDW   NO. 19
chain     YFNVWGAGTTVTVSAASTKGPSVFPLAPSSKSTSGGTAALGCLVKDYFPEPVT
          VSWNSGALTSGVHTFPAVLQSSGLYSLSSVVTVPSSSLGTQTYICNVNHKPSN
          TKVDKKAEPKSCDKTHTCPPCPAPELLGGPSVFLFPPKPKDTLMISRTPEVTC
          VVVDVSHEDPEVKFNWYVDGVEVHNAKTKPREEQYNSTYRVVSVLTVLHQDWL
          NGKEYKCKVSNKALPAPIEKTISKAKGQPREPQVYTLPPSRDELTKNQVSLTC
          LVKGFYPSDIAVEWESNGQPENNYKTTPPVLDSDGSFFLYSKLTVDKSRWQQG
          NVFSCSVMHEALHNHYTQKSLSLSPGK BAT4306F  DIVMTQTPLSLPVTPGEPASISCRSSKSLLHSNGITYLYWYLQKPGQSPQLLI      SEQ ID
light     YQMSNLVSGVPDRFSGSGSGTDFTLKISRVEAEDVGVYYCAQNLELPYTFGGG   NO. 20
chain     TKVEIKR BAT4306F  QVQLVQSGAEVKKPGSSVKVSCKASGYAFSYSWINWVRQAPGQGLEWMGRIFP      SEQ ID
heavy     GDGDTDYNGKFKGRVTITADKSTSTAYMELSSLRSEDTAVYYCARNVFDGYWL   NO. 21
chain     VYWGQGTLVTVSSASTKGPSVFPLAPSSKSTSGGTAALGCLVKDYFPEPVTVS
          WNSGALTSGVHTFPAVLQSSGLYSLSSVVTVPSSSLGTQTYICNVNHKPSNTK
          VDKKVEPKSCDKTHTCPPCPAPELLGGPSVFLFPPKPKDTLMISRTPEVTCVV
          VDVSHEDPEVKFNWYVDGVEVHNAKTKPREEQYNSTYRVVSVLTVLHQDWLNG
          KEYKCKVSNKALPAPIEKTISKAKGQPREPQVYTLPPSRDELTKNQVSLTCLV
          KGFYPSDIAVEWESNGQPENNYKTTPPVLDSDGSFFLYSKLTVDKSRWQQGNV
          FSCSVMHEALHNHYTQKSLSLSPGK BAT4406F  EIVLTQSPATLSLSPGERATLSCRASQSVSSYLAWYQQKPGQAPRLLIYDASN      SEQ ID
light     RATGIPARFSGSGSGTDFTLTISSLEPEDFAVYYCQQRSNWPITFGQGTRLEI   NO. 22
chain     KRTVAAPSVFIFPPSDEQLKSGTASVVCLLNNFYPREAKVQWKVDNALQSGNS
          QESVTEQDSKDSTYSLSSTLTLSKADYEKHKVYACEVTHQGLSSPVTKS
          FNRGEC BAT4406F  EVQLVESGGGLVQPGRSLRLSCAASGFTFNDYAMHWVRQAPGKGLEWVSTISW      SEQ ID
heavy     NSGSIGYADSVKGRFTISRDNAKKSLYLQMNSLRAEDTALYYCAKDIQYGNYY   NO. 23
chain     YGMDVWGQGTTVTVSSASTKGPSVFPLAPGSSKSTSGTAALGCLVKDYFPEPV
          TVSWNSGALTSGVHTFPAVLQSSGLYSLSSVVTVPSSSLGTQTYICNVNHKPS
          NTKVDKKVEPKSCDKTHTCPPCPAPELLGGPSVFLFPPKPKDTLMISRTPEVT
          CVVVDVSHEDPEVKFNWYVDGVEVHNAKTKPREEQYNSTYRVVSVLTVLHQDW
          LNGKEYKCKVSNKALPAPIEKTISKAKGQPREPQVYTLPPSRDELTKNQVSLT
          CLVKGFYPSDIAVEWESNGQPENNYKTTPPVLDSDGSFFLYSKLTVDKSRWQQ
          GNVFSCSVMHEALHNHYTQKSLSLSPGK BAT0206F  DIQMTQSPSSLSASVGDRVTITCQASQDISNYLNWYQQKPGKAPKLLIYDASN      SEQ ID
light     LETGVPSRFSGSGSGTDFTFTISSLQPEDIATYFCQHFDHLPLAFGGGTKVEI   NO. 24
chain     KRTVAAPSVFIFPPSDEQLKSGTASVVCLLNNFYPREAKVQWKVDNALQSGNS
          QESVTEQDSKDSTYSLSSTLTLSKADYEKHKVYACEVTHQGLSSPVTKSFNRG
          EC BAT0206F  QVQLQESGPGLVKPSETLSLTCTVSGGSVSSGDYYWTWIRQSPGKGLEWIGHI      SEQ ID
heavy     YYSGNTNYNPSLKSRLTISIDTSKTQFSLKLSSVTAADTAIYYCVRDRVTGAF   NO. 25
chain     DIWGQGTTVTVSSACTKGPSVFPLAPSSKSTSGGTAALGCLVKDYFPEPVTVS
          WNSGALTSGVHTFPAVLQSSGLYSLSSVVTVPSSSLGTQTYICNVNHKPSNTK
          VDKKVEPKSCDKTHTCPPCPAPELLGGPSVFLFPPKPKDTLMISRTPEVTCVV
          VDVSHEDPEVKFNWYVDGVEVHNAKTKPREEQYNSTYRVVSVLTVLHQDWLNG
          KEYKCKVSNKALPAPIEKTISKAKGQPREPQVYTLPPSRDELTKNQVSLTCLV
          KGFYPSDIAVEWESNGQPENNYKTTPPVLDSDGSFFLYSKLTVDKSRWQQGNV
          FSCSVMHEALHNHYTQKSLSLSPGK TABLE 1-continued Sequence table

| | | |
|---|---|---|
| BAT0808 light chain | DIQLTQSPSSLSASVGDRVSITCKASQDVSIAVAWYQQKPGKAPKLLIYSASY RYTGVPDRFSGSGSGTDFTLTISSLQPEDFAVYYCQQHYITPLTFGAGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC | SEQ ID NO. 26 |
| BAT0808 Heavy chain | QVQLQQSGSELKKPGASVKVSCKASGYTFTNYGMNWVKQAPGQGLKWMGWINT YTGEPTYTDDFKGRFAFSLDTSVSTAYLQISSLKADDTAVYFCARGGFGSSYW YFDVWGQGTLVTVSSCSTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTC VVVDVSHEDPEVKFNWYVDGVEVHNAKTKPREEQYNSTYRVVSVLTVLHQDWL NGKEYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRWQQG NVFSCSVMHEALHNHYTQKSLSLSPGK | SEQ ID NO. 27 |
| CHO-BAT-KF Exon1 | ATGCGGGCATGGACTGGTTCCTGGCGTTGGATTATGCTCATTCTTTTTGCCTG GGGGACCTTATTGTTTTATATAGGTGGTCATTTGGTTCGAGATAATGACCACC CTGACCATTCTAGCAGAGAACTCTCCAAGATTCTTGCAAAGCTGGAGCGCTTA AACAACAAAATGAAGACTTGAGGAGAATGGCTGAGTCTCTCCGG | SEQ ID NO. 28 |

Example 3. Functional Effectiveness Analysis of FUT8 TALEN Protein

Figure 3:
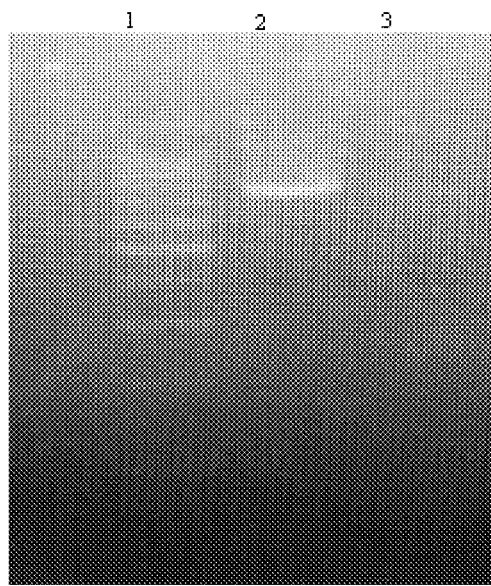
FIG. 3 shows an electrophoretogram for functional verification of TALEN protein. The electrophoresis chart of wild-type cells is located in the left side. After gene editing, expectedly, the PCR products of cell genome showed two bands of 500 BP and 750 BP, while that of the wild type only showed a single band of 750 BP. This proves that the Talen protein pair is functional. Lane 1: 100 bp marker; Lane 2: wt; Lane 3: pool.

CEL-I enzyme is a nuclease that can recognize the mismatched bases in double-stranded DNA and cut the double-stranded DNA from the mismatches. If the target sequence is edited by FUT8TALEN, the fragment containing the target sequence amplified from the maternal genome and the fragment containing the target sequence amplified from the transformed cell genome are mixed together for denaturation and annealing, the annealed double-stranded DNA will appear base mismatch. In this case, CEL-I enzyme can cut off the annealed double-stranded DNA, and two bands appear as a result of agarose electrophoresis. $5\times10^5$ CHO-BAT cells were seeded into a 6-well plate on the day before transfection, and the medium was DMEM/F12 containing 10% fetal calf serum. Plasmids L130N and R184N were transiently transfected into cells according to the methods provided in the reagent instructions. 3 days after transfection, the cells were harvested by centrifugation and the genome was extracted with the genome extraction kit. Using this as a template, PCR reaction was carried out with the primers L130 for (SEQ ID NO. 1) and primer L130rev (SEQ ID NO. 2). The PCR amplification of the fragment of the parent cell containing the target sequence was the same as above. 20 μL of two PCR products were mixed together, heated to 94° C. and then naturally cooled to room temperature. Added 0.5 μl of CEL-I enzyme to 200 ng annealed DNA, and incubated at 42° C. for 30 min, and ran the PCR reaction product on agarose gel electrophoresis. The reaction product was analyzed by agarose electrophoresis, and the results are as shown in FIG. 3.

The results show that, compared with the wild type, the gene-edited PCR products displayed two bands of 500 bp and 750 bp, while the wild type only had a single band of 750 bp, which is consistent with the expected results. This proves that TALEN protein pairs are functional.

Example 4. Effect of FUT8 TALEN Protein on Antibody Fucose Content

Figure 4:
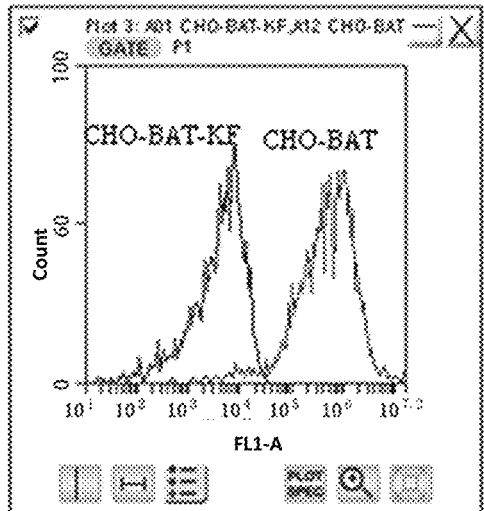
FIG. 4 shows the cells growing on 24-well plates analyzed by FACS, wherein the gene-edited cell clones labeled with FITC-labeled LCA bind the negative cells, and the wild-type cells labeled with FITC-labeled LCA bind the cells positively.

To determine whether the host genome adjusted by the designed FUT8 TALEN protein affects the carbohydrate chain of the produced antibody (whether the fucose content changes or not), L130N and R184N plasmids are transiently transformed into previously established cell lines stably expressing anti-CD20 antibodies. The methods provided in lipofectamine 2000 (Invitrogen) reagent description was taken and briefly described as follows. In a 10 cm cell culture dish, 24 μL of liposomes packed with 4 μg of plasmid DNA of L130N and R184N were added to $1\times10^6$ cells. After transfection for two days, the medium was replaced into DMEM/F12 medium containing 10% (V/V) FBS (GBICO) and 400 μg/mL LCA (Vector). After one week, most of the cells became round and suspended in the medium, while others grew normally on the wall. The supernatant was discarded, and LCA-resistant cells were digested with trypsin 0.25% (v/v), and resuspended in DMEM/F12 medium containing 10% (v/v) FBS after centrifugation. The cells were seeded in the 96-well plate at a density of 0.5 per well. After two weeks, monoclonal cells were selected and transferred to a 24-well plate. FACS was adopted to analyze the cells grown on a 24-well plate, and FITC labeled LCA bound to negative cells (FIG. 4) were propagated to produce antibodies. The oligosaccharide content of antibodies produced by the two cells was determined by Biodonor, and the results are shown in FIG. 5.

The results show that the fucose content of antibody was reduced when plasmids L130 and R184 were transiently transformed into antibody-producing cells.

Example 5. Establishment of Genome-Modified Host Cells

In order to establish a genome-modified CHO-K1 cell so that it can be the host cells used as proteins and fucose-free antibodies, the plasmids L130 and R184 were transiently transformed into CHO-K1 cell lines. The screening of monoclonal cells against LCA was described in example 3. The genome of candidate cell clones was extracted respectively, PCR reaction was carried out with the primer L130 for (see Table 1, SEQ ID NO. 1) and the primer L130rev (see Table 1, SEQ ID NO. 2), and CEL-1 base mismatch analysis was carried out on PCR amplification products of fragments containing target sequences of candidate cell clones. If the candidate clone was heterozygous, then the agarose electrophoresis after CEL-1 enzyme digestion showed two bands; instead, if the candidate clone was homozygous, then the annealed fragment could not be cleaved through CEL-1 enzyme digestion, and the agarose electrophoresis showed one band. The PCR fragment was cloned directly into a T vector (pGEM-T Easy Vector) and then sequenced. The sequencing result was compared with the sequence of the parent cell in this fragment as shown in FIG. 6. Then, according to the comparison result, two genome-edited homozygotes were selected and designated as CHO-2G8, CHO-1D6.

Example 6: Evaluation of Growth Characteristics of Host Cells

Figure 7:
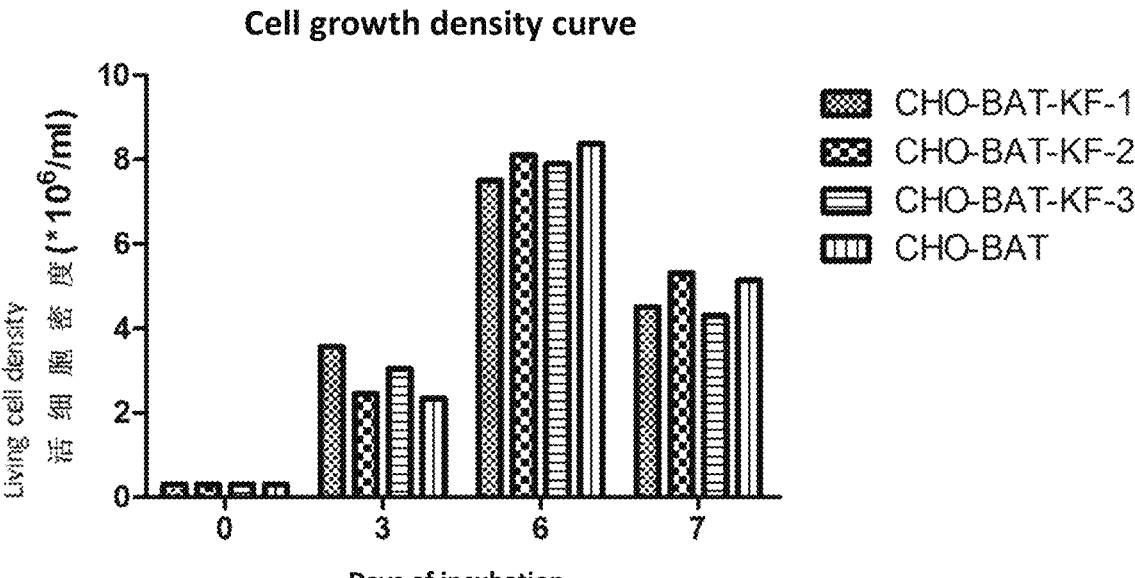
FIG. 7 shows the comparison of the growth density of CHO-BAT-KF to the parent cell CHO-BAT.
Figure 8:
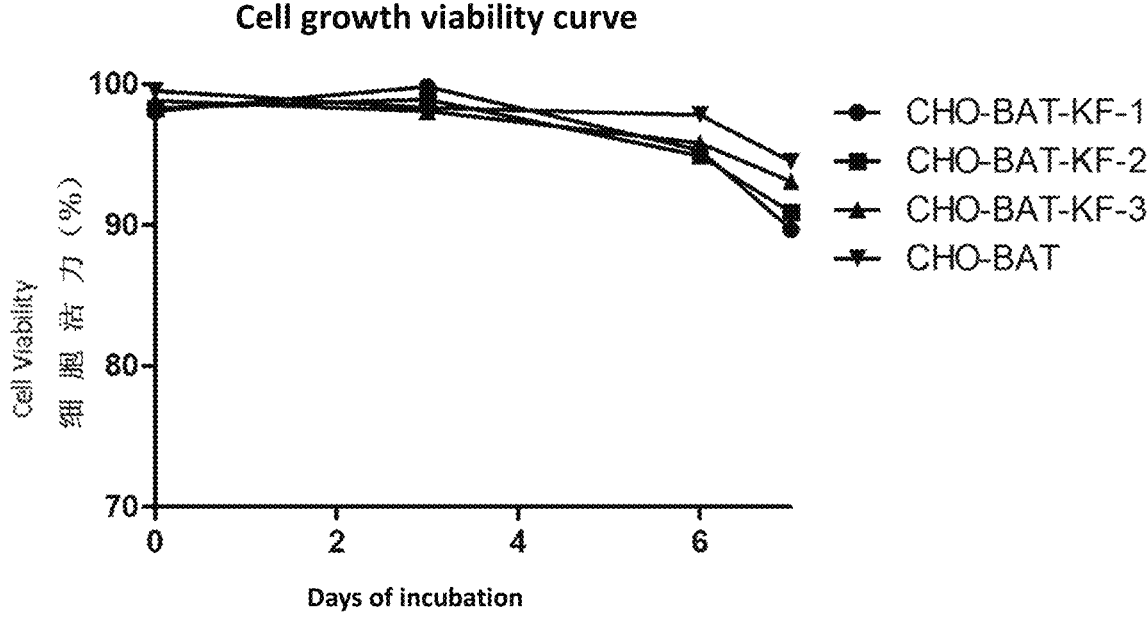
FIG. 8 shows the comparison of the growth viability of CHO-BAT-KF to the parent cell CHO-BAT.

The FUT8 gene knockout cloned CHO-2G8 was selected as the host cell and renamed as CHO-BAT-KF. Three CHO-BAT-KFs and one CHO-BAT were respectively seeded in 30 mL CD CHO AGT™ with a final concentration of 6 mM Gln in a 125 mL shake flask at the cell density of 300000/ml, and 0.5 mL of cells were taken at d0, d3, d6 and d7, respectively, to measure the cell density and cell viability and evaluate the change of cell growth characteristics after the FUT8 gene was knocked out. The cell growth density is shown in FIG. 7 and the cell growth viability is shown in FIG. 8. As can be seen from FIG. 7 and FIG. 8, no significant difference was observed in growth density and viability between FUT8 gene knock-out CHO-BAT-KF and CHO-BAT cells with FUT8 gene not knocked out.

Figure 9:
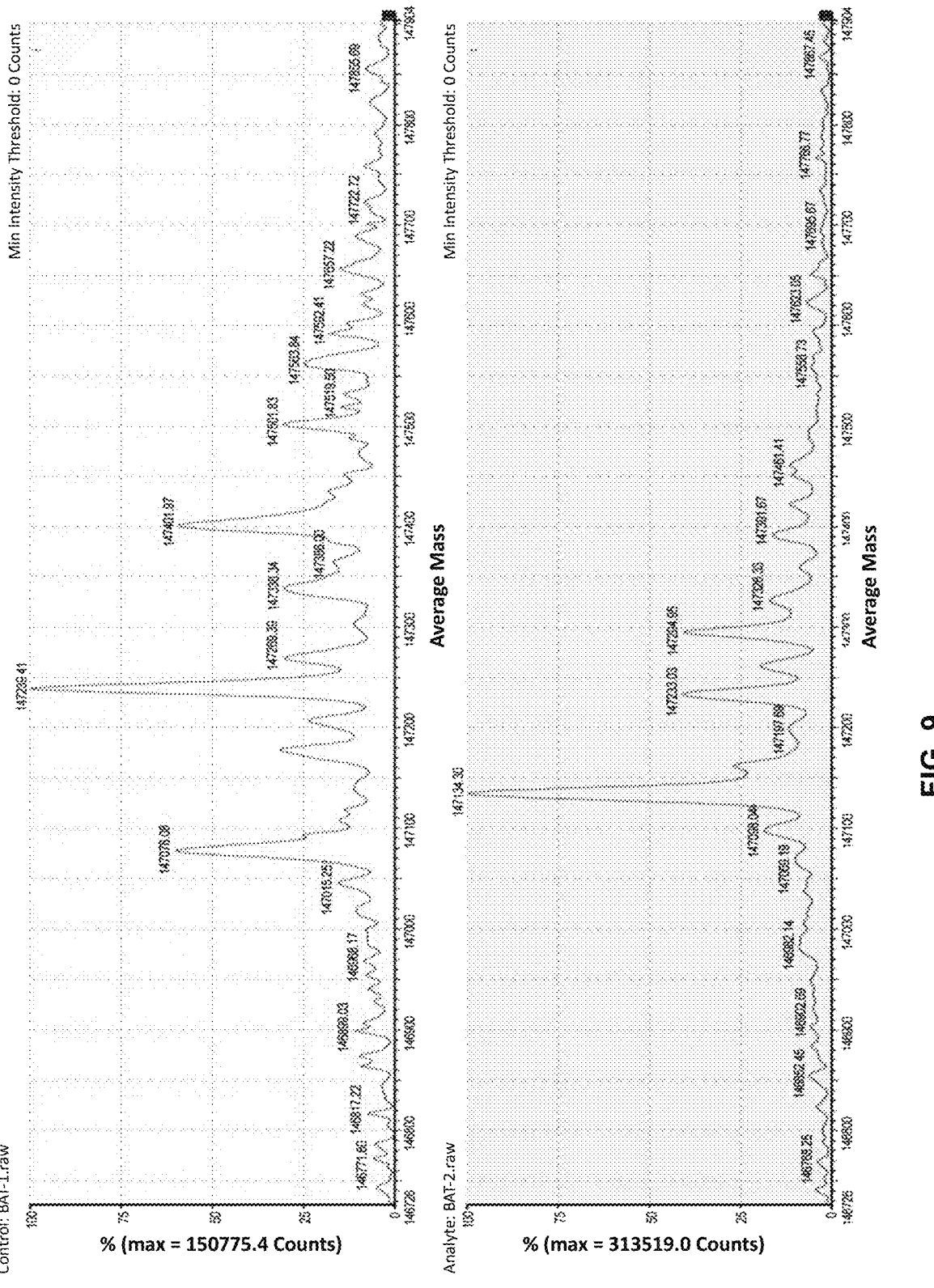
FIG. 9 shows analysis of N-polysaccharides from BAT4306F and 4306 antibody molecules performed by MALDI-TOF MS. Each N-polysaccharide from BAT4306F was one fucose less than that from 4306. The chart on the left is the antibody molecules 4306 produced by parent cells and the chart on the right is BAT4306F antibody molecules.

Example 7. Analysis of Glycosylation Profile of Antibodies Produced by Host Cells In order to determine that the carbohydrate chain of the antibody produced by the genome-modified CHO-2G8 cell line according to the present invention has aberrant N-polysaccharide modification, BAT4306F produced by CHO-2G8 cells and 4306 produced by CHO-K1 cells were purified from the medium through a protein A affinity column and quantified by UV280. Desalinated monoclonal antibody (1 mg) was incubated with PNGaseF overnight at 37° C. to release N-glycan from the antibody. The released N-glycan was separated from the antibody by 30K Amicon ultrafiltration, lyophilized and resuspended in 200 μL deionized water. MALDI-TOF MS was used to analyze N-polysaccharides from two antibody molecules as described above. Oligosaccharides from the antibody BAT4306F produced by CHO-2G8 existed in a single peak and were basically the same population, which was different from the profile of the antibody 4306 oligosaccharides produced by parent host cells (FIG. 9).

The results show that the three peaks of N-polysaccharide of 4306 were G0F, G1F and G2F, respectively. Based on the peak time and molecular weight of N-polysaccharide from BAT4306F, it was inferred that the three peaks of N-polysaccharide are G0, G1 and G2; that was, each N-polysaccharide from BAT4306F was one fucose less than the N-polysaccharide from 4306.

Figure 10:
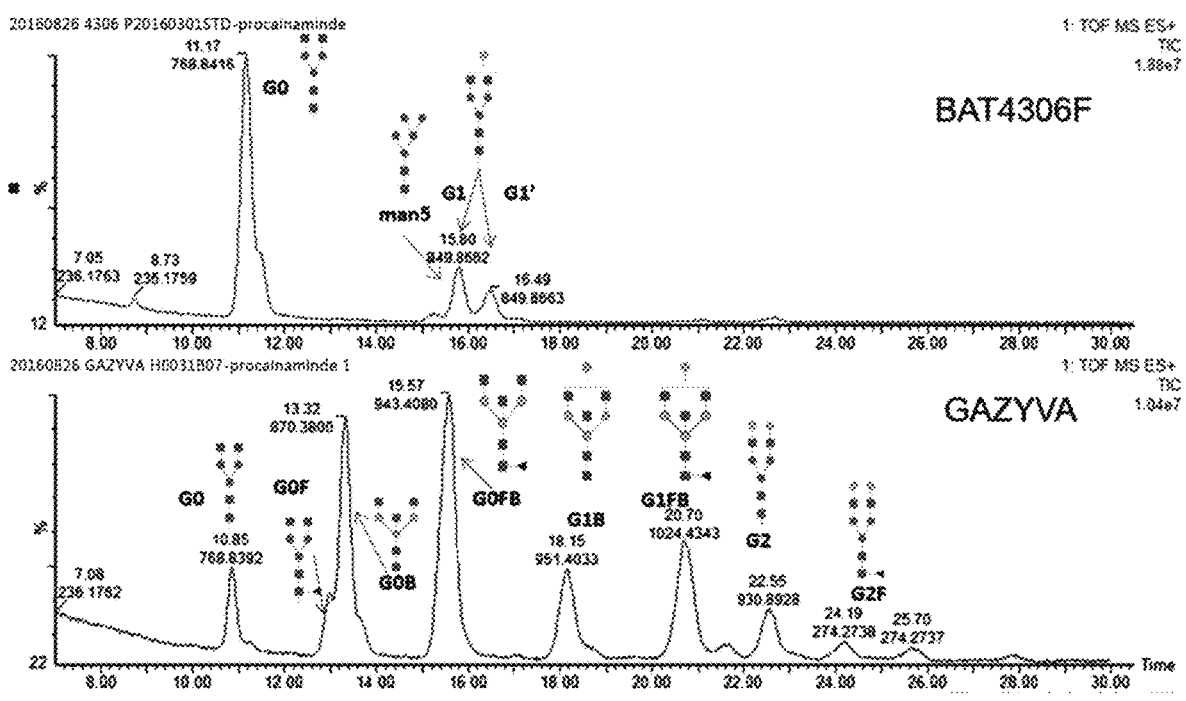
FIG. 10 shows that BAT4306F has lower fucose content, lower carbohydrate chain heterogeneity and better product uniformity than GAZYVA (Obinutuzumab).

At the same time, commercially available Gazyva was compared with the carbohydrate chains of BAT4306F to analyze the heterogeneity of their carbohydrate chains, as shown in FIG. 10. The results show that BAT4306F had lower N-polysaccharide heterogeneity and a more uniform carbohydrate chain. The glycotypes of different antibodies expressed in CHO-BAT-KF cells were analyzed as shown in Table 4.

Example 8. Analysis of ADCC Activity of Antibodies Produced by Host Cells

In order to determine whether the modification of the antibody having the N-polysaccharide of the present invention can improve its biological function (e.g., ADCC activity), the purified antibodies targeting CD20 are used to determine their ADCC activity in vitro (LDH method promega). The BAT4306F antibody produced by CHO-2G8 was purified through protein A affinity column and was quantified by UV280. The parent unmodified 4306 was expressed in wild-type CHO cells and purified in the same way. To carry out ADCC detection, the wil2-S cells were cultured in RPMI-1640 medium containing 10% FBS in good condition (4-7 days). Centrifuged cells in logarithmic growth phase at 1000 rpm for 10 min to remove supernatant. Added solution A (RPMI-1640 culture medium without phenol red and containing 10% FBS) and mixed well, centrifuged twice as above, counted, adjusted the number of cells to $3\times10^5$ cells/ml with solution A, and added it to U-96 cell culture plate at 100 μl per well. Adjusted the final concentration of antibody to 1.2, 0.24, 0.048, 0.0096, 0.00192, 0.000384, 0.0000768 and 0.00001536 (μg/mL) sequentially. Incubated at 37° C. for 30 min in a 5% $CO_2$ incubator. Collected the effector cells PBMC, added solution B (RPMI-1640 culture medium without serum and phenol red) and centrifuged twice as above, counted, adjusted the number of cells to $3\times10^5$ cells/ml with solution B, and added it to the U-96 cell culture plate at 50 μl per well. Incubated at 37° C. for 3 h in a 5% $CO_2$ incubator. When there was still 45 min from the incubation time of 3 h, added 20 μl of lysate to the well of maximum release target cell, and then incubated in a 5% $CO_2$ incubator at 37° C. for 45 min. Placed the U-96 well cell culture plate in a centrifuge and centrifuged at 250 g for 4 min. Taken 50 μl/well supernatant to another 96-well plate with flat bottom, added 50 μl/well of prepared chromogenic fluid, gently shaken and mixed, and reacted for 30 min at room temperature without light. Added 50 μl/well of the stop solution and gently shaken and mixed. Read the results at the microplate reader OD490.

Figure 11:
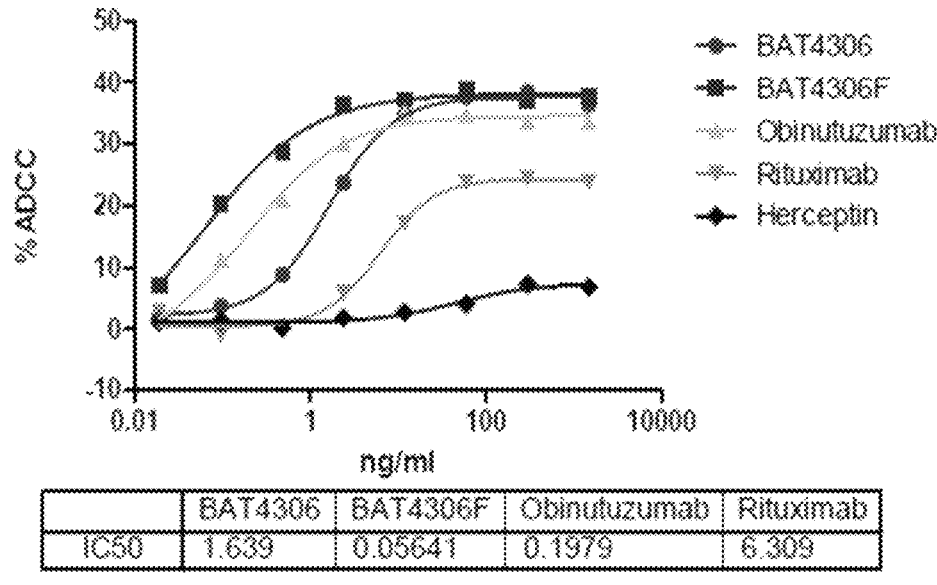
FIG. 11 shows the comparison of ADCC effects among anti-CD20 antibodies such as BAT4306 wild type, carbohydrate chain modified BAT4306F, Obinutuzumab and Rituximab using Raji as target cells and PBMC as effector cells.

The results show that, compared with non-modified 4306 produced by the parent CHO cells, BAT4306F of N-polysaccharide produced by CHO-2G8 cell cloning in serum-free medium significantly increased ADCC activity on Raji cells and wil2-S cells (FIG. 11).

Example 9. Analysis of Affinity of Antibodies Produced by Host Cells to CD20

In order to determine whether the antibody with modified N-polysaccharide produced by the cell according to the present invention has an effect on the ability to bind CD20-positive cells, BAT4306F and 4306 were verified by the FASC method by reference to Klervi Even-Desrumeaux et al. (2012), and the affinity of Rituximab to CD20 on different cell surfaces was compared, as described briefly below; collected Wil2-s cells in the logarithmic growth phase, centrifuged at 800 rpm for 5 min, and discarded supernatant. Washed once with PBS, calculated density, resuspended in PBS, and packed into 1.5 mL centrifuged tubes to make 500,000 cells per tube. Centrifuged at 1200 rpm for 5 min and discard supernatant. Prepared the antibody at concentrations of 30, 3.33, 1.11, 0.37, 0.1, 0.04, 0.014 and 0.0046 μg/mL, respectively, added 200 μl of antibody to the cells sequentially, resuspended the cells and mixed evenly. At the same time, added PBS of the same volume as the negative control. Kept away from light at 4° C. for 2 h. Centrifuged at 1200 rpm for 5 min, discarded supernatant and washed once with PBS. Added 100 μl of PBS to resuspend cells, added 2 μl of secondary antibody of FITC-sheep anti-human IgG1 Fab, and kept in dark place at 4° C. for 30 min. Centrifuged at 1200 rpm for 5 min, discarded supernatant and washed once with PBS. Detected with the C6 flow cytometer. Based on the formula Kd=[Ab]*{Fmax/(F−Fback)−1}, the results are shown in the following table.

TABLE 2

Statistical results of $IC_{50}$ and Kd values of antibody-to-cell binding experiments

| | BAT4306F | | 4306 | | Rituximab |
| | Raji | Wil2-s | Raji | Wil2-s | RajiWil2-s |
| --- | --- | --- | --- | --- | --- |
| $IC_{50}$(μg/mL) | 0.481 | 0.815 | 0.631 | 0.603 | 1.9982.513 |
| $IC_{50}$(nM) | 3.21 | 5.43 | 4.21 | 4.02 | 13.3216.75 |
| Kd(nM) | 3.17 | 5.22 | 4.15 | 3.96 | 12.6816.02 |
| Mean Kd(nM) | | 4.19 | 4.06 | | 14.35 |

The results show that the modified antibody of N-polysaccharide did not affect the affinity of the antibody to CD20.

Figure 12:
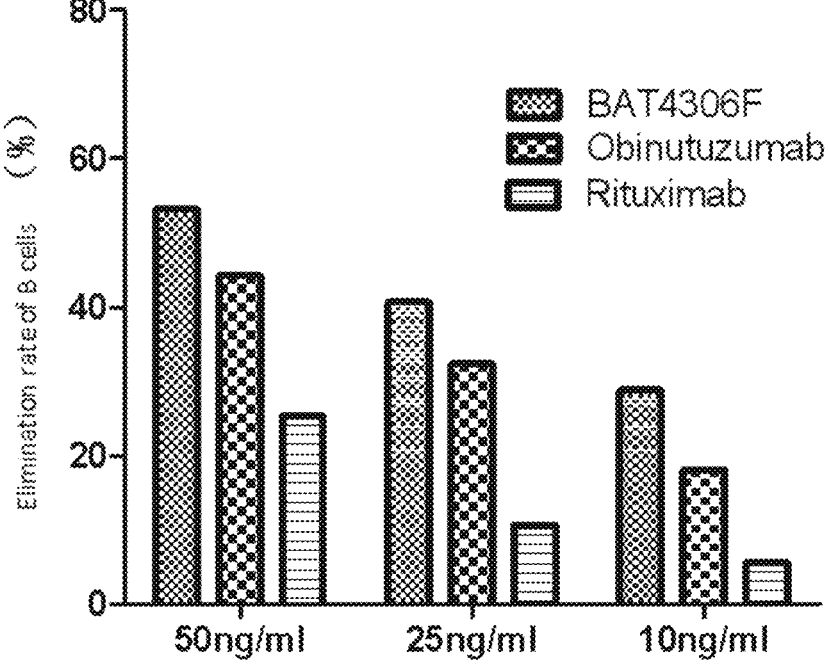
FIG. 12 shows the comparison of the ability among three carbohydrate chain modified antibodies BAT4306F, Obinutuzumab and rituximab to deplete B cells in whole blood in vitro at concentrations of 50, 25, and 10 ng/mL.

Example 10. The Ability of BAT4306F to Deplete B Cells in Whole Blood of Different NHL Patients Based on In Vitro Evaluation Although the mechanisms of anti-CD20 antibody in B lymphoma patients include ADCC, CDC and directly induced B cell apoptosis, the effect of an anti-CD20 antibody is ultimately reflected in its ability to remove B cells in patients, instead of merely improving a certain mechanism of action. In order to determine whether the antibody with N-polysaccharide modification of the present invention can improve its ability to remove B cells, the biological function of BAT4306F to deplete B cells in whole blood of different NHL patients was evaluated in vitro, as briefly described below: collected 3 ml of blood from newly diagnosed NHL patients in a heparin sodium anticoagulant tube; stored at room temperature and waited for the researcher to take away; taken 90 μL of blood samples into new FACS tubes; added 10 μL of BAT4306F antibody dilutions with different concentrations to each sample tube so that the final concentration of the antibody in each test sample tube was 10 nM, 1 nM, 0.1 nM, 0.01 nM and 0.001 nM respectively; stood in a 37° C. incubator for 3-4 h, then taken 50 μL of blood samples from each tube and added them to BD TruCount tubes, and added BD's B cell count antibody mixture (anti-CD45 (lymphocyte population), anti-CD3 (T cells) and anti-CD19 (B cells)) to the blood sample; placed in a dark place at room temperature for 15 min, added BD FACS lysate and then measured it on the instrument (BD C6). The results are shown in FIG. 12.

The results show that BAT4306F had stronger ability to remove B cells than antibody Rituximab without N-polysaccharide modified in the three concentration levels tested.

Example 11. Enhanced Affinity of BAT4306F to FcγRIIIa Molecule

In order to verify that the recombinant antibody with unique glycan profile produced by the genome-edited CHO-BAT-KF cells has enhanced affinity with FcγRIIIA, the affinity of BAT4306F, commercially available GAZYVA and Rituximab to FcγRIIIA was measured. The sensor was pre-wetted in PBS for 10 min. The biotin-labeled FcγRIIIa 158V and FcγRIIIa 158F were diluted to 2.5 μg/mL with AB solution. Loading: loaded in the biotin-labeled FcγRIIIa 158V diluent for 10 min (load to signal about 1.3 nM); 3.6.3 affinity test with FcγRIIIa 158V: diluted the test drugs BAT4306F and Obinutuzumab to 500 nM with AB solution, diluted the test drug Rituximab to 3000 nM with AB solution, and then prepared 7 concentrations with the same buffer solution at 2× gradient. AB solution, FcγRIIa V158, regeneration buffer, drug diluent and neutralization buffer were sequentially added to the corresponding columns of a 96-well plate. The SA sensor operates as follows: Baseline: detected the baseline in AB, 150 s; Association: combined in the gradient concentration of drug diluent sample and blank (AB) for 90 s; Dissociation: dissociated in AB for 120 s; Regeneration: regenerated in NaOH (pH 10.5) for 5 s; Neutralization: neutralized in AB for 5 s. The regeneration and neutralization cycles were carried out for 3 times. The collected data were analyzed by the instrument data analysis software Acquisition 8.2. Taking Baseline acquisition signal as a baseline and subtracting the reference signal (double deduction of sample blank and sensor blank), the data were subject to group analysis and fitted.

TABLE 3

Statistics of affinity BAT4306F to FcγRIIIa 158F

| | FcγRIIIa 158V | | FcγRIIIa 158F | |
| | KD(M) | CV % | KD(M) | CV % |
| --- | --- | --- | --- | --- |
| BAT4306F | 2.57E−08 | 0.027 | 1.37E−07 | 0.878 |
| Obinutuzumab | 3.68E−08 | 10.483 | 2.26E−07 | 3.062 |
| Rituxiamb | 8.44E−07 | 3.79 | 1.19E−06 | 0.297 |

The results show that, among the three tested antibodies, the recombinant antibody with unique glycan profile produced by CHO-BAT-KF cells had the strongest affinity to FcγRIIIA

Example 12

Figure 13:
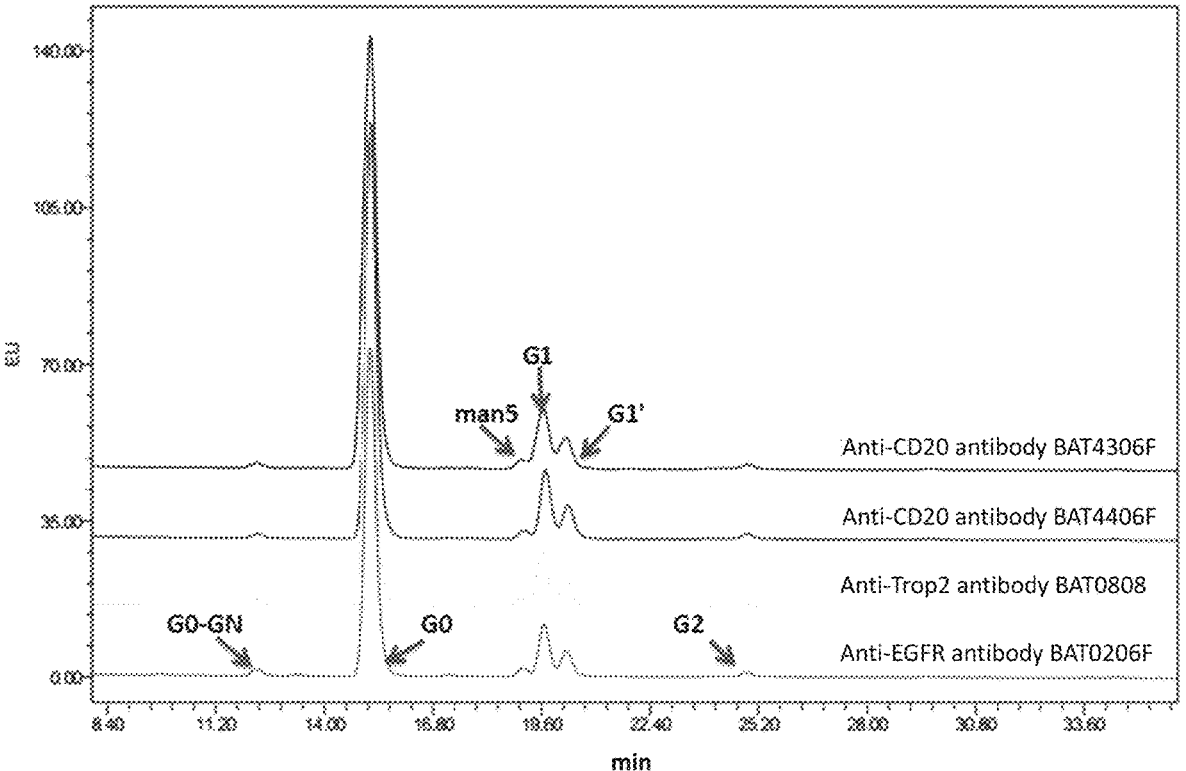
FIG. 13 shows the comparison of the glycan profile among the anti-CD20 antibodies BAT4306F and BAT4406F, the anti-EGFR antibody BAT0206F, and the anti-Trop2 antibody BAT0808 produced by CHO-BAT-KF cells.

In order to verify that the glycan profile of the antibody produced by the expression of other antibody sequences in the CHO-BAT-KF host cell is stable and consistent, several other antibodies were expressed in the CHO-BAT-KF cell, including BAT4406F antibody with two light chains as shown in SEQ ID NO. 22 and two heavy chains as shown in SEQ ID NO. 23, BAT0206F antibody with two light chains as shown in SEQ ID NO. 24 and two heavy chains as shown in SEQ ID NO. 25, and Trop2 antibody BAT0808 with two light chains as shown in SEQ ID NO. 26 and two heavy chains as shown SEQ ID NO. 27. The specific experiment was carried out by reference to the product specification (LudgerTag™ PROC (procainamide) Glycan Labeling Kit). The sample was denatured and reduced, and its carbohydrate chain was removed from the glycosylation site by glycosidase. Then, after coupling labeled with procainamide hydrochloride fluorescein, the sample was separated on a HILIC column, 100 mM ammonium formate (pH 4.5) and acetonitrile were eluted with a mobile phase A and a mobile phase B respectively with an elution gradient of 0-36 minutes from 28% A-38% A, and finally detected with a fluorescence detector. The resolution of glycotypes G1 and G1' in the system suitability solution was not less than 1.0. The results in FIG. 13 and Table 4 show that the glycotypes of the four antibodies were highly consistent and the carbohydrate chains was uniform; which indicated that the method or cell of the present invention had universal applicability, and could be not only suitable for the production of anti-CD20 antibodies, but also used for the production of antibodies at other sites, thus allowing the target antibody to present uniformity and enhanced ADCC activity.

TABLE 4

| Glycotype ratio (%) of four antibodies produced by CHO-BAT-KF cells | | | | | | |
|---|---|---|---|---|---|---|
| | G0-GN | G0 | Man5 | G1 | G1' | G2 | Other |
| BAT4306F | 0.36 | 71.32 | 0.40 | 16.04 | 8.14 | 1.96 | 1.78 |
| BAT4406F | 0.42 | 72.31 | 0.45 | 15.51 | 7.88 | 1.83 | 1.60 |
| BAT0808 | 0.52 | 79.11 | 0.51 | 11.36 | 6.11 | 1.03 | 1.36 |
| BAT0206F | 0.45 | 76.15 | 0.50 | 12.90 | 6.90 | 1.36 | 1.74 |

What is claimed is:

1. An antibody having specificity to CD20 and comprising two light chains each comprising the amino acid sequence of SEQ ID NO: 22 and two heavy chains each comprising the amino acid sequence of SEQ ID NO: 23, wherein the antibody contains no fucose and has a G0 content greater than or equal to 60% and less than or equal to 80%.

2. The antibody of claim 1, which has a mannose content that is less than or equal to 5%.

3. A pharmaceutical composition, comprising the antibody of claim 1 and a pharmaceutically acceptable carrier.

* * * * *